US011192856B2

(12) United States Patent
Chen et al.

(10) Patent No.: US 11,192,856 B2
(45) Date of Patent: Dec. 7, 2021

(54) PROCESS FOR PREPARING ALPHA-CARBOXAMIDE PYRROLIDINE DERIVATIVES

(71) Applicant: Biogen Inc., Cambridge, MA (US)

(72) Inventors: Weirong Chen, Cambridge, MA (US); Vinny Couming, Cambridge, MA (US); Erwin Irdam, Cambridge, MA (US); William F. Kiesman, Cambridge, MA (US); Daw-Long A. Kwok, Cambridge, MA (US); Tamera L. Mack, Cambridge, MA (US); Suzanne M. Opalka, Cambridge, MA (US); Daniel B. Patience, Cambridge, MA (US); Donald G. Walker, Littleton, MA (US); Wenli Liang, Cambridge, MA (US)

(73) Assignee: Biogen Inc., Cambridge, MA (US)

( * ) Notice: Subject to any disclaimer, the term of this patent is extended or adjusted under 35 U.S.C. 154(b) by 0 days.

(21) Appl. No.: 16/753,680

(22) PCT Filed: Oct. 5, 2018

(86) PCT No.: PCT/US2018/054661
§ 371 (c)(1),
(2) Date: Apr. 3, 2020

(87) PCT Pub. No.: WO2019/071162
PCT Pub. Date: Apr. 11, 2019

(65) Prior Publication Data
US 2020/0270206 A1    Aug. 27, 2020

Related U.S. Application Data

(60) Provisional application No. 62/568,651, filed on Oct. 5, 2017.

(51) Int. Cl.
*C07D 207/16* (2006.01)

(52) U.S. Cl.
CPC .................. *C07D 207/16* (2013.01)

(58) Field of Classification Search
CPC .................................................. C07D 207/16
See application file for complete search history.

(56) References Cited

U.S. PATENT DOCUMENTS

| | | | |
|---|---|---|---|
| 3,164,597 A | 1/1965 | Leonard | |
| 4,981,996 A | 1/1991 | Wyss et al. | |
| 5,236,957 A | 8/1993 | Dostert et al. | |
| 6,201,016 B1 | 3/2001 | Cai et al. | |
| 6,306,903 B1 | 10/2001 | Pevarello et al. | |
| 6,951,861 B1 | 10/2005 | Alvaro et al. | |
| 7,655,693 B2 | 2/2010 | Alvaro et al. | |
| 7,855,218 B2 | 12/2010 | Alvaro et al. | |
| 8,093,268 B2 | 1/2012 | Alvaro et al. | |
| 10,421,716 B2 * | 9/2019 | MacPherson | ........ C07D 207/16 |
| 2004/0097578 A1 | 5/2004 | Jolidon et al. | |
| 2004/0235752 A1 | 11/2004 | Pitt et al. | |
| 2005/0234065 A1 | 10/2005 | Hulin et al. | |
| 2008/0269208 A1 | 10/2008 | Alvaro et al. | |
| 2008/0280969 A1 | 11/2008 | Alvaro et al. | |
| 2008/0293753 A1 | 11/2008 | Alvaro et al. | |
| 2008/0306122 A1 | 12/2008 | Alvaro et al. | |
| 2016/0280644 A1 | 9/2016 | Askew et al. | |
| 2020/0270206 A1 | 8/2020 | Chen et al. | |

FOREIGN PATENT DOCUMENTS

| | | |
|---|---|---|
| EP | 1524265 A | 4/2005 |
| WO | WO-9809938 A1 | 3/1998 |
| WO | WO-9833762 A1 | 8/1998 |
| WO | WO-00/57877 A1 | 10/2000 |
| WO | WO-0200593 A2 | 1/2002 |
| WO | WO-2004/026826 A1 | 4/2004 |
| WO | WO-04/083189 A1 | 9/2004 |
| WO | WO-04/092140 A1 | 10/2004 |
| WO | WO-04/094395 A2 | 11/2004 |
| WO | WO-05/000309 A2 | 1/2005 |
| WO | WO-2005/040108 A1 | 5/2005 |
| WO | WO-2005/110982 A2 | 11/2005 |
| WO | WO-2006/119390 A1 | 11/2006 |
| WO | WO-2006/119451 A1 | 11/2006 |
| WO | WO-2006/124865 A2 | 11/2006 |
| WO | WO-2007/042239 A1 | 4/2007 |
| WO | WO-2007/042240 A1 | 4/2007 |
| WO | WO-2007/042250 A1 | 4/2007 |
| WO | WO-2008/090114 A1 | 7/2008 |
| WO | WO-2008/090115 A1 | 7/2008 |
| WO | WO-2008/090116 A1 | 7/2008 |

(Continued)

OTHER PUBLICATIONS

Angelini et al., "Multistep flow procedure for the waste-minimized preparation of N-Boc-beta-Amino ketones," J Flow Chem, 41(1):40-43 (2014).
Banker et al., "Modern Pharmaceutics," 3rd edition, Marcel Dekker, New York, p. 451 and 596 (1996).
Da et al., "Highly catalytic asymmetric addition of deactivated alkyl grignard reagents to aldehydes," Organic Letters, 11(24):5578-5581 (2009).
Finelli et al., "Expanding the toolbox of asymmetric organocatalysis by continuous-flow process," Chem Commun, 51:3708-3722 (2015).
Fournie-Zaluski et al., "Design of Orally Active Dual Inhibitors of Neutral Endopeptidase Angiotensin-converting Enzyme with Long Duration Action," J Med Chem, 39: 2594-2608 (1996).

(Continued)

*Primary Examiner* — Sun Jae Yoo

(74) *Attorney, Agent, or Firm* — Foley Hoag LLP; David P. Halstead; Lucas P. Watkins

(57) ABSTRACT

The invention relates to a novel process for preparing a-carboxamide pyrrolidine derivatives, in particular (2S, 5R)-5-(4-((2-fluorobenzyl)oxy)phenyl)pyrrolidine-2-carboxamide, and to novel intermediates for use in said process along with processes for preparing said intermediates.

19 Claims, No Drawings

(56) References Cited

FOREIGN PATENT DOCUMENTS

| WO | WO-2008/090117 A1 | 7/2008 |
| WO | WO-2008/122546 A1 | 10/2008 |
| WO | WO-2011/029762 A1 | 3/2011 |
| WO | WO-2011/0155337 A1 | 12/2011 |
| WO | WO-2012/063252 A2 | 5/2012 |
| WO | WO-2016/102967 A1 | 6/2016 |
| WO | WO-2019/071162 A3 | 4/2019 |
| WO | WO-2020/210485 A1 | 10/2020 |
| WO | WO-2020/210486 A1 | 10/2020 |

OTHER PUBLICATIONS

Gavezzotti et al., "Are Crystal Structures Predictable?," Accounts Chem Res, 27: 309-314 (1994).

Gibson et al., "Selective Removal of an N-BOC Protecting Group in the Presence of a tert-Butyl Ester and Other Acid-Sensitive Groups," J. Org. Chem., 59(11): 3216-3218 (1994).

International Search Report and Written Opinion for International Application No. PCT/US18/54661 dated Dec. 27, 2018.

International Search Report and Written Opinion for International Application No. PCT/US2020/027459 dated Jun. 22, 2020.

International Search Report and Written Opinion for International Application No. PCT/US2020/027460 dated Jun. 24, 2020.

Kanemasa et al., "Stereoselective Michael Addition of the Imines of Alpha-Amino Esters in the Presence of Lithium Bromide/1,8-Diazabicyclo-[5.4.0]undec-7-ene," J Org Chem, 55(14): 4411-4417(1990).

Lygo et al., "Co-catalyst Enhancement of Enantioselective PTC Michael Additions Involving Glycine Imines," Tetrahedron Lett, 50(26): 3363-3365 (2009).

Mancheño et al., "Chiral Copper Complexes of Phosphino Sulfenyl Ferrocenes as Efficient Catalysts for Enantioselective Formal Aza Diels—Alder Reactions of N-Sulfonyl Imines," J Am Chem Soc, 126: 456-457 (2004).

McManus et al., "Recent Developments in the Application of Oxazoline-Containing Ligands in Asymmetric Catalysis," Chem Rev, 104: 4151-4202 (2004).

Morissette et al., "High-throughput Crystallization: Polymorphs, Salts, Co-Crystals and Solvates of Pharmaceutical Solids," Adv Drug Deliver Rev, 56: 275-300 (2004).

Murray et al., "Continuous flow-processing of organometallic reagents using an advanced peristaltic pumping system and the telescoped flow synthesis of (E/Z).Tamoxifen," Organic Process Research and Development, 17:1192-1208 (2013).

Patterson et al., "An Initial Report of a New Biological Marker for Bipolar Disorder: P85 Evoked Brain Potential," Bipolar Disord, 11 (6): 569-609 (2009).

Shao et al., "Phenoxyphenyl Pyridines as Novel State-Dependent, High-Potency Sodium Channel Inhibitors," J Med Chem, 47(17): 4277-4285 (2004).

Vippagunta et al., "Crystalline Solids," Adv Drug Deliv Rev, 48: 3-26 (2001).

Wolff, "Burger's Medicinal Chemistry," 5th edition, Part 1, John Wiley & Sons, p. 975-977 (1995).

Xu et al., "Asymmetric Synthesis of cis-2,5-disubsituated pyrrolidine, the core scaffold of b3-AR agonists," Organic Letters, 15(6):1342-1345 (2013).

Extended European Search Report for EP Application No. EP 18864468.6 dated Mar. 3, 2021.

\* cited by examiner

PROCESS FOR PREPARING ALPHA-CARBOXAMIDE PYRROLIDINE DERIVATIVES

RELATED APPLICATIONS

This application is a National Stage of International Patent Application No. PCT/US2018/054661, filed Oct. 5, 2018, which claims the benefit of U.S. Provisional Patent Application No. 62/568,651, filed on Oct. 5, 2017.

FIELD OF THE INVENTION

The invention relates to a novel process for preparing α-carboxamide pyrrolidine derivatives, in particular (2S, 5R)-5-(4-((2-fluorobenzyl)oxy)phenyl)pyrrolidine-2-carboxamide, and to novel intermediates for use in said process along with processes for preparing said intermediates.

BACKGROUND OF THE INVENTION (2S, 5R)-5-(4-((2-fluorobenzyl)oxy)phenyl)pyrrolidine-2-carboxamide:

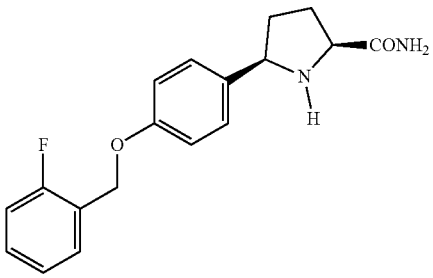 [SMILES: NC(=O)[C@@H]1CC[C@H](c2ccc(OCc3ccccc3F)cc2)N1]

is described in WO 2007/042239 as having utility in the treatment of diseases and conditions mediated by modulation of use-dependent voltage-gated sodium channels. The synthetic preparation of (2S, 5R)-5-(4-((2-fluorobenzyl)oxy)phenyl)pyrrolidine-2-carboxamide is described in both WO 2007/042239 and WO 2011/029762.

However, there is a need for the development of alternative processes for the preparation of such α-carboxamide pyrrolidine derivatives, which are capable of practical application to large scale manufacture.

SUMMARY OF THE INVENTION

According to a first aspect of the invention, there is provided a process for preparing a compound of formula (I) which comprises:

(i) preparing a compound of formula (VI) from a compound of formula (IV) by reacting the compound of formula (IV) with a compound of formula (V):

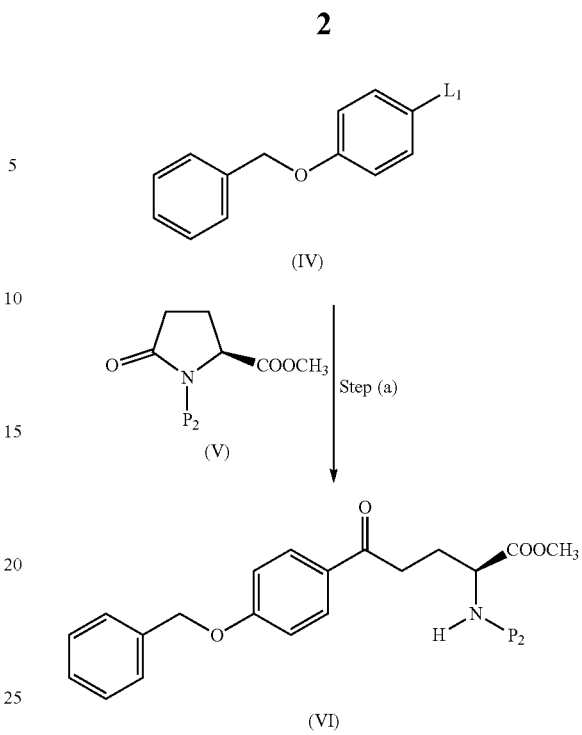

wherein $P_2$ is a suitable protecting group selected from: tert-butyloxycarbonyl (BOC); 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps and trifluoroacetyl and $L^1$ represents a suitable leaving group; followed by (ii) preparing a compound of formula (VII) from a compound of formula (VI):

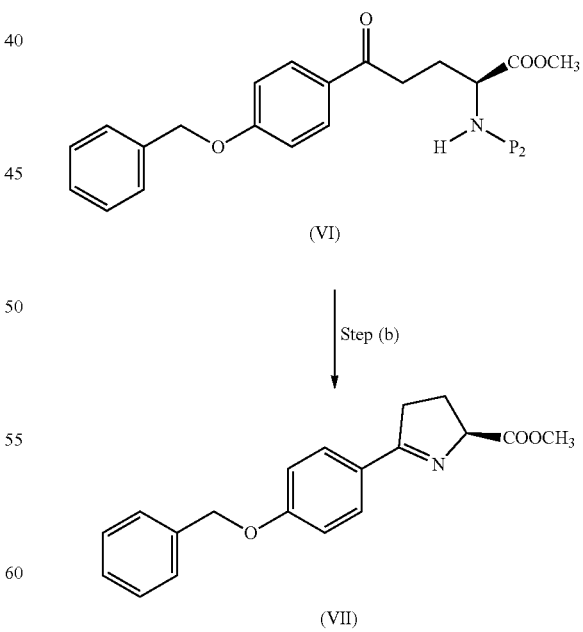

wherein $P_2$ is as defined hereinbefore; followed by (iii) preparing a compound of formula (VIII) from a compound of formula (VII):

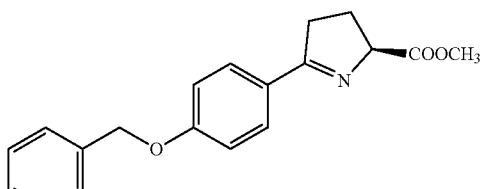

(VII)

Step (c) ↓

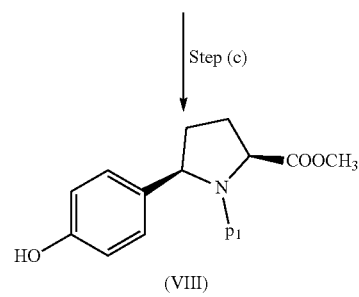

(VIII)

wherein P₁ is as defined hereinbefore for P₂; followed by
(iv) preparing a compound of formula (II) by reacting a compound of formula (VIII) with a compound of formula (IX):

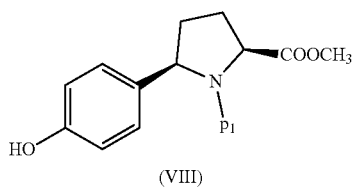

(VIII)

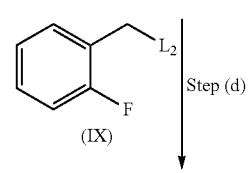

(IX)

Step (d) ↓

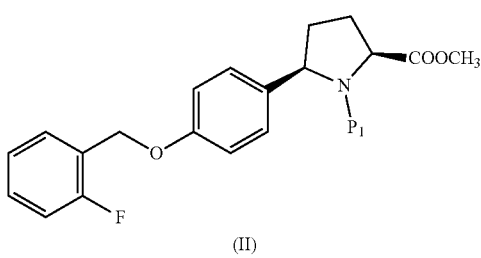

(II)

wherein P₁ is as defined hereinbefore for P₂ and L₂ represents a suitable leaving group; followed by
(v) preparing a compound of formula (I) by reacting a compound of formula (II) with formamide:

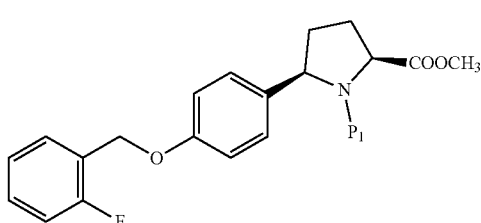

(II)

HCONH₂ | Step (e) ↓

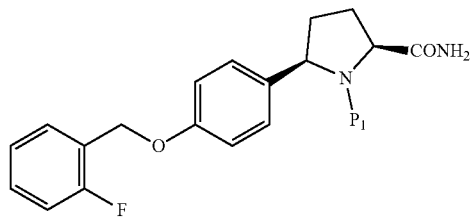

(I)

wherein P¹ is as defined hereinbefore for P₂.

According to a further aspect of the invention, there is provided a compound of formula (I):

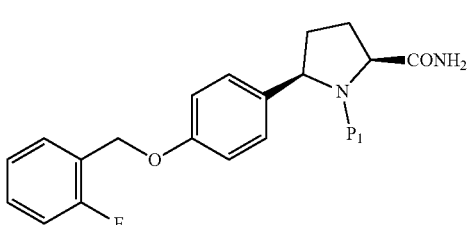

(I)

wherein P₁ represents a suitable protecting group selected from: 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps and trifluoroacetyl.

According to a further aspect of the invention, there is provided a process for preparing a compound of formula (III)ᵃ which comprises:
(i) preparing a compound of formula (VI) from a compound of formula (IV) by reacting the compound of formula (IV) with a compound of formula (V):

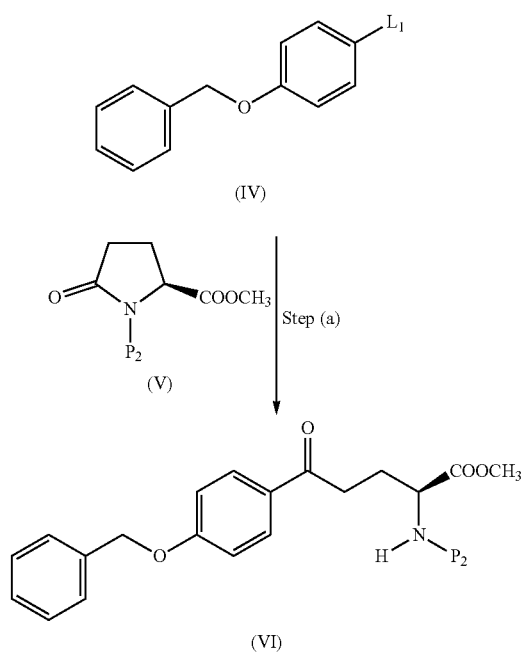

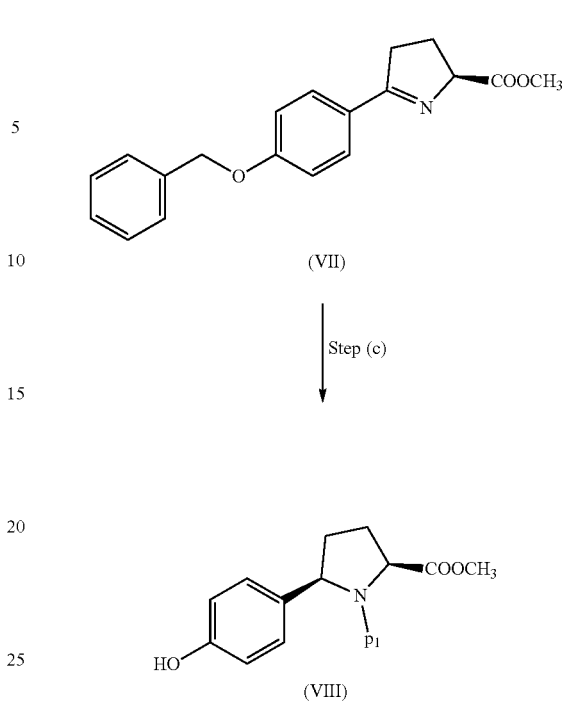

wherein $P_2$ is a suitable protecting group selected from: tert-butyloxycarbonyl (BOC); 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps and trifluoroacetyl (Alternatively, in certain embodiments, $P_2$ is benzyloxycarbonyl) and $L^1$ represents a suitable leaving group; followed by (ii) preparing a compound of formula (VII) from a compound of formula (VI):

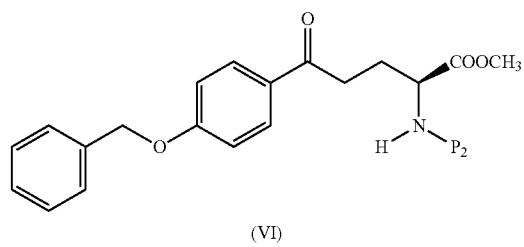

wherein $P_2$ is as defined hereinbefore; followed by (iii) preparing a compound of formula (VIII) from a compound of formula (VII):

wherein $P_1$ is as defined hereinbefore for $P_2$; followed by (iv) preparing a compound of formula (II) by reacting a compound of formula (VIII) with a compound of formula (IX):

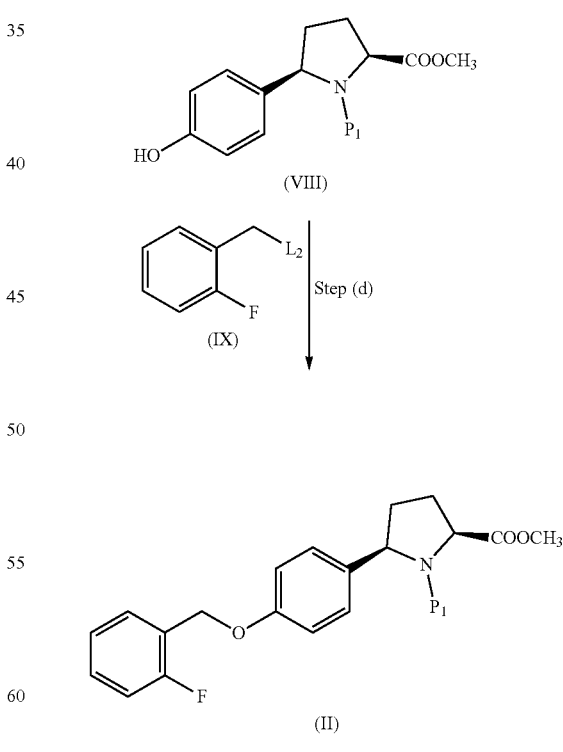

wherein $P_1$ is as defined hereinbefore for $P_2$ and $L_2$ represents a suitable leaving group; followed by (v) preparing a compound of formula (I) by reacting a compound of formula (II) with formamide:

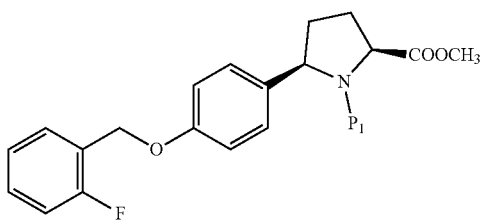

(II)

HCONH₂ | Step (e)

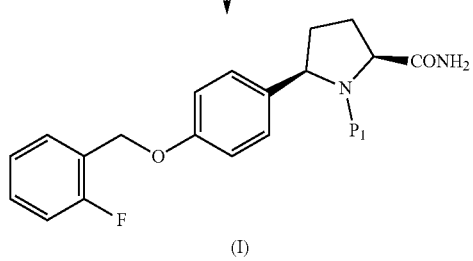

(I)

wherein $P_1$ is as defined hereinbefore for $P_2$; followed by (vi) preparing a compound of formula (III)$^a$ by deprotecting a compound of formula (I):

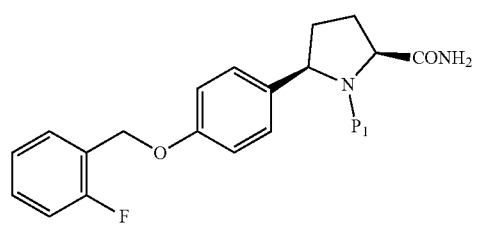

(I)

Step (f)

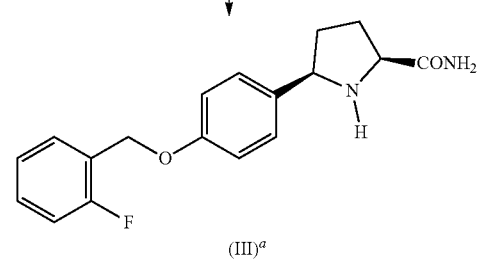

(III)$^a$ wherein $P_1$ is as defined hereinbefore for $P_2$.

DETAILED DESCRIPTION OF THE INVENTION

According to a first aspect of the invention, there is provided a process for preparing a compound of formula (I) which comprises:

(i) preparing a compound of formula (VI) from a compound of formula (IV) by reacting the compound of formula (IV) with a compound of formula (V):

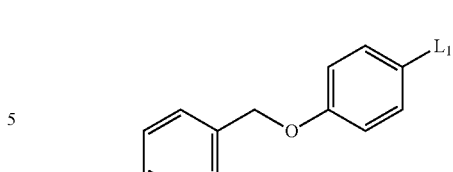

(IV)

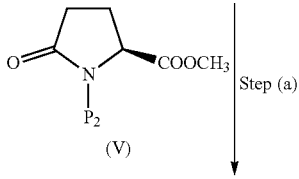

(V)

Step (a)

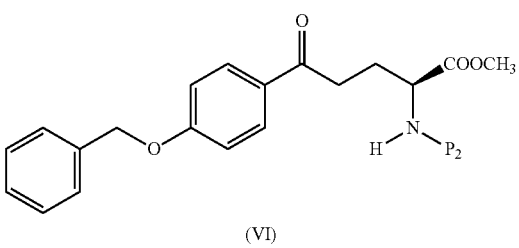

(VI)

wherein $P_2$ is a suitable protecting group selected from: tert-butyloxycarbonyl (BOC); 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps and trifluoroacetyl and $L^1$ represents a suitable leaving group; followed by (ii) preparing a compound of formula (VII) from a compound of formula (VI):

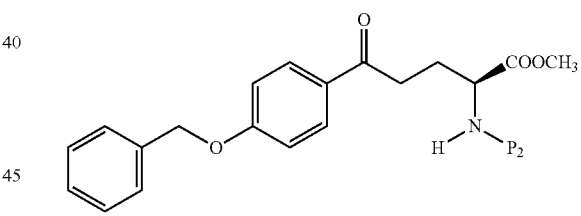

(VI)

Step (b)

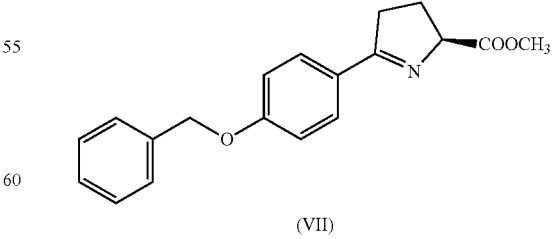

(VII)

wherein $P_2$ is as defined hereinbefore; followed by (iii) preparing a compound of formula (VIII) from a compound of formula (VII):

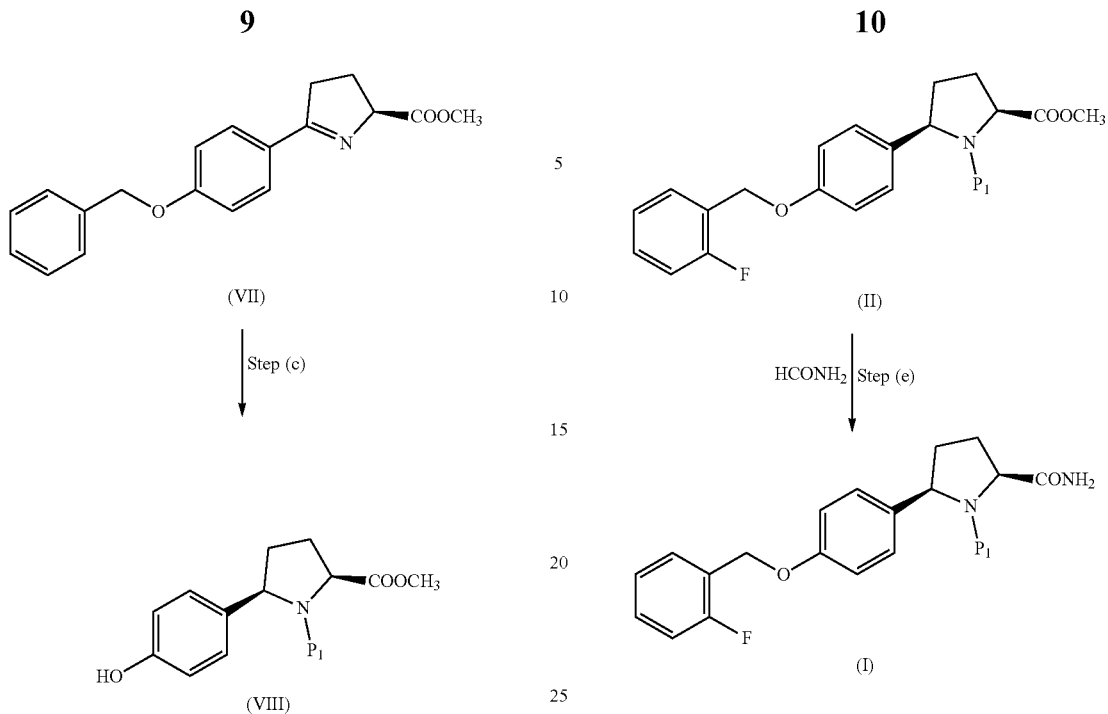

wherein $P_1$ is as defined hereinbefore for $P_2$; followed by (iv) preparing a compound of formula (II) by reacting a compound of formula (VIII) with a compound of formula (IX):

wherein $P_1$ is as defined hereinbefore for $P_2$ and $L_2$ represents a suitable leaving group; followed by (v) preparing a compound of formula (I) by reacting a compound of formula (II) with formamide:

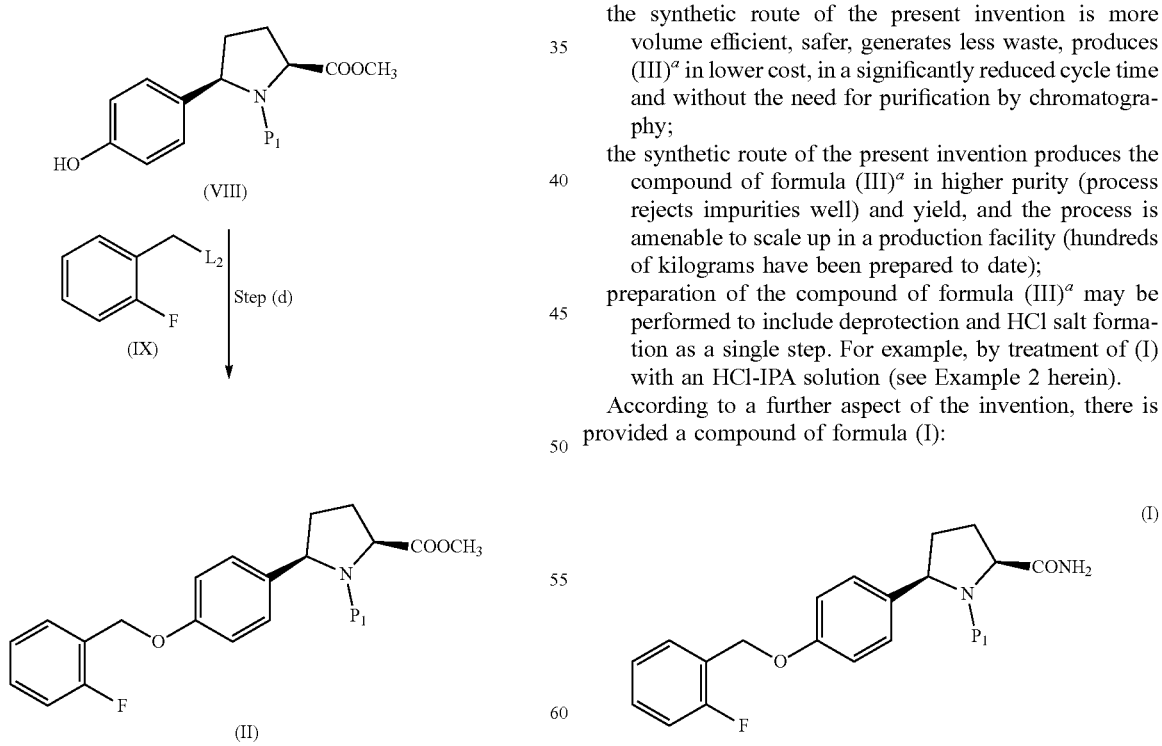

wherein $P_1$ is as defined hereinbefore for $P_2$.

The process of the present invention provides a number of advantages. For example, in comparison with the previously described synthetic route for preparing the compound of formula (III)$^a$:

- the intermediate of compound of formula (II) is not isolated in the synthetic route of the present invention;
- the synthetic route of the present invention is more volume efficient, safer, generates less waste, produces (III)$^a$ in lower cost, in a significantly reduced cycle time and without the need for purification by chromatography;
- the synthetic route of the present invention produces the compound of formula (III)$^a$ in higher purity (process rejects impurities well) and yield, and the process is amenable to scale up in a production facility (hundreds of kilograms have been prepared to date);
- preparation of the compound of formula (III)$^a$ may be performed to include deprotection and HCl salt formation as a single step. For example, by treatment of (I) with an HCl-IPA solution (see Example 2 herein).

According to a further aspect of the invention, there is provided a compound of formula (I):

wherein $P_1$ represents a suitable protecting group selected from: 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps and trifluoroacetyl.

According to a further aspect of the invention, there is provided a process for preparing a compound of formula (I) which comprises preparing a compound of formula (I) by reacting a compound of formula (II) with formamide:

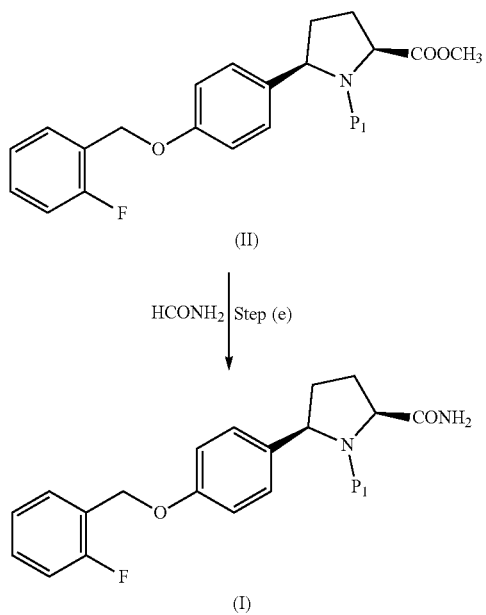

wherein $P^1$ is as defined hereinbefore for $P_2$.

The compound of formula (I) represents a valuable intermediate in the preparation of α-carboxamide pyrrolidine derivatives, such as the compound of formula (III). Thus, according to a further aspect of the invention, there is provided the use of a compound of formula (I)

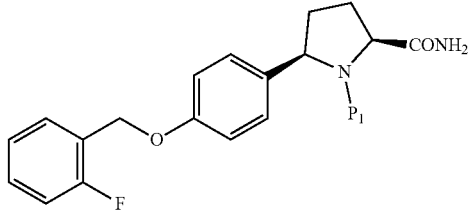

wherein $P_1$ represents a suitable protecting group selected from: tert-butyloxycarbonyl (BOC); 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps and trifluoroacetyl or the use of a compound obtainable by the process as defined herein, as an intermediate in the preparation of a compound of formula (III):

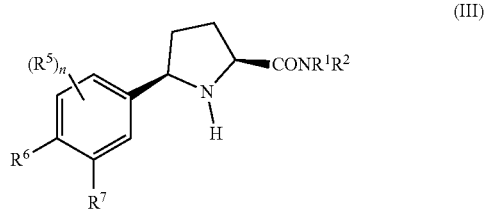

wherein $R^1$ and $R^2$ are independently hydrogen, $C_{1-6}$ alkyl or $C_{3-6}$ cycloalkyl$C_{1-6}$ alkyl; or such $R^1$ and $R^2$, together with the nitrogen to which they are attached, may form an unsubstituted 3-, 4-, 5- or 6-membered saturated ring;

n is 0, 1 or 2, wherein when present each $R^5$ is independently selected from the list consisting of $C_{1-3}$ alkyl, halogen, cyano, halo$C_{1-3}$ alkyl, hydroxy, $C_{1-3}$ alkoxy and $C_{1-3}$ haloalkoxy; either $R^6$ or $R^7$ is —O—$R^8$, —OCHR$^9$R$^8$, —NCH$_2$R$^8$ or —(CH$_2$)$_2$R$^8$ wherein the other $R^6$ or $R^7$ is hydrogen or $R^5$; and wherein $R^8$ is a phenyl ring or wherein the phenyl ring is optionally substituted by one or more groups independently selected from the list consisting of $C_{1-3}$ alkyl, halogen, cyano, halo$C_{1-3}$ alkyl, hydroxy, $C_{1-3}$ alkoxy and $C_{1-3}$ haloalkoxy; and $R^9$ is hydrogen or $C_{1-3}$ alkyl.

It will be appreciated that the compound of formula (III) may be isolated as a free base or an acid addition salt depending on the reaction conditions.

In one embodiment, the compound of formula (III) is a compound wherein:

$R^1$ and $R^2$ are independently hydrogen, $C_{1-6}$ alkyl or $C_{3-6}$ cycloalkyl$C_{1-6}$ alkyl; or such $R^1$ and $R^2$, together with the nitrogen to which they are attached, may form an unsubstituted 3-, 4-, 5- or 6-membered saturated ring;

n is 0;

$R^6$ is —O—$R^8$ or —OCHR$^9$R$^8$;

$R^7$ is hydrogen;

$R^8$ is a phenyl ring optionally substituted by one or more groups independently selected from the list consisting of $C_{1-3}$ alkyl, halogen, cyano, halo$C_{1-3}$ alkyl, hydroxy, $C_{1-3}$ alkoxy and $C_{1-3}$ haloalkoxy; and $R^9$ is hydrogen or $C_{1-3}$ alkyl.

The compound of formula (I) represents a valuable intermediate in the preparation of the compound of formula (III)$^a$, thus, in a further embodiment, the compound of formula (III) is a compound of formula (III)$^a$:

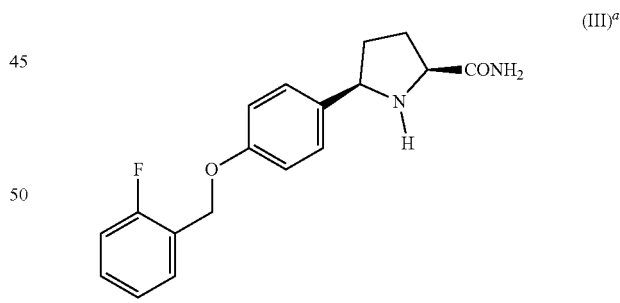

i.e. (2S, 5R)-5-(4-((2-fluorobenzyl)oxy)phenyl)pyrrolidine-2-carboxamide.

It will be appreciated that the compound of formula (III)$^a$ may be isolated as a free base or an acid addition salt depending on the reaction conditions.

According to a further aspect of the invention, there is provided a process for preparing a compound of formula (III)$^a$ which comprises:

(i) preparing a compound of formula (VI) from a compound of formula (IV) by reacting the compound of formula (IV) with a compound of formula (V):

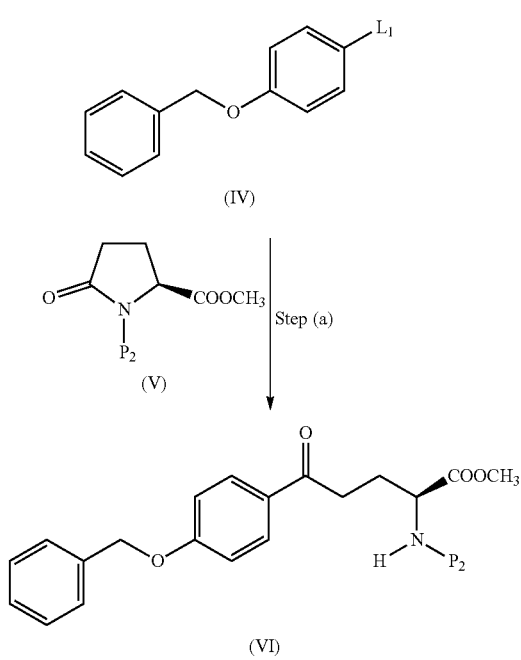

(IV)

(V)

Step (a)

(VI)

wherein $P_2$ is a suitable protecting group selected from: tert-butyloxycarbonyl (BOC); 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps and trifluoroacetyl and $L^1$ represents a suitable leaving group; followed by (ii) preparing a compound of formula (VII) from a compound of formula (VI):

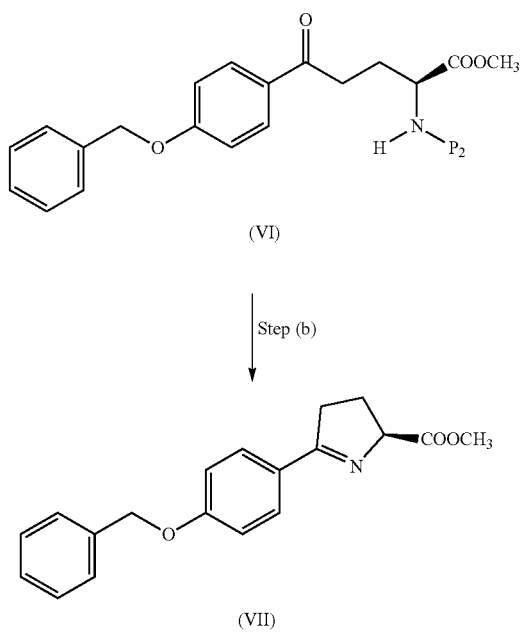

(VI)

Step (b)

(VII)

wherein $P_2$ is as defined hereinbefore; followed by (iii) preparing a compound of formula (VIII) from a compound of formula (VII):

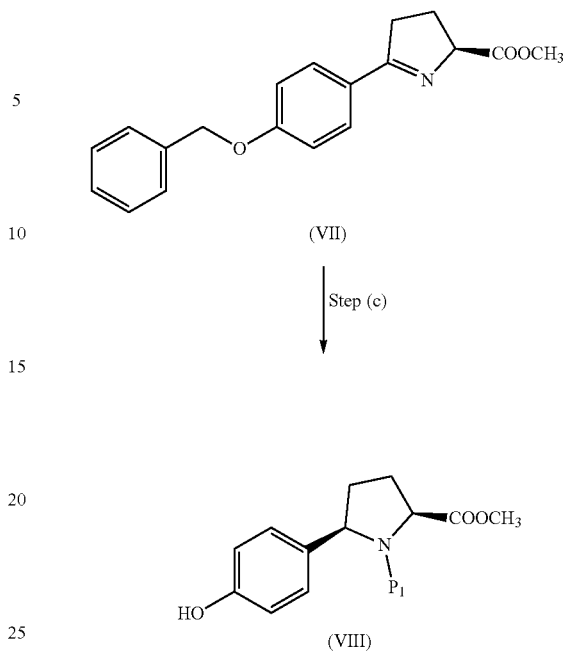

(VII)

Step (c)

(VIII)

wherein $P_1$ is as defined hereinbefore for $P_2$; followed by (iv) preparing a compound of formula (II) by reacting a compound of formula (VIII) with a compound of formula (IX):

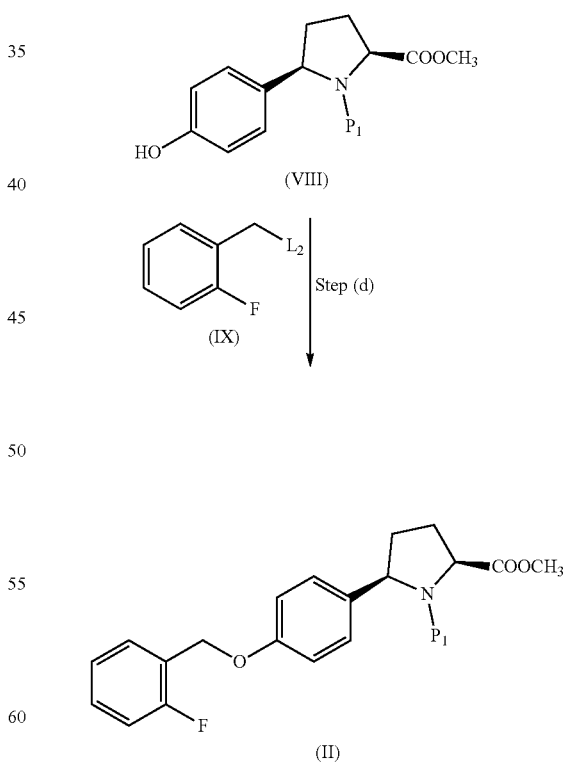

(VIII)

(IX)

Step (d)

(II)

wherein $P_1$ is as defined hereinbefore for $P_2$ and $L_2$ represents a suitable leaving group; followed by (v) preparing a compound of formula (I) by reacting a compound of formula (II) with formamide:

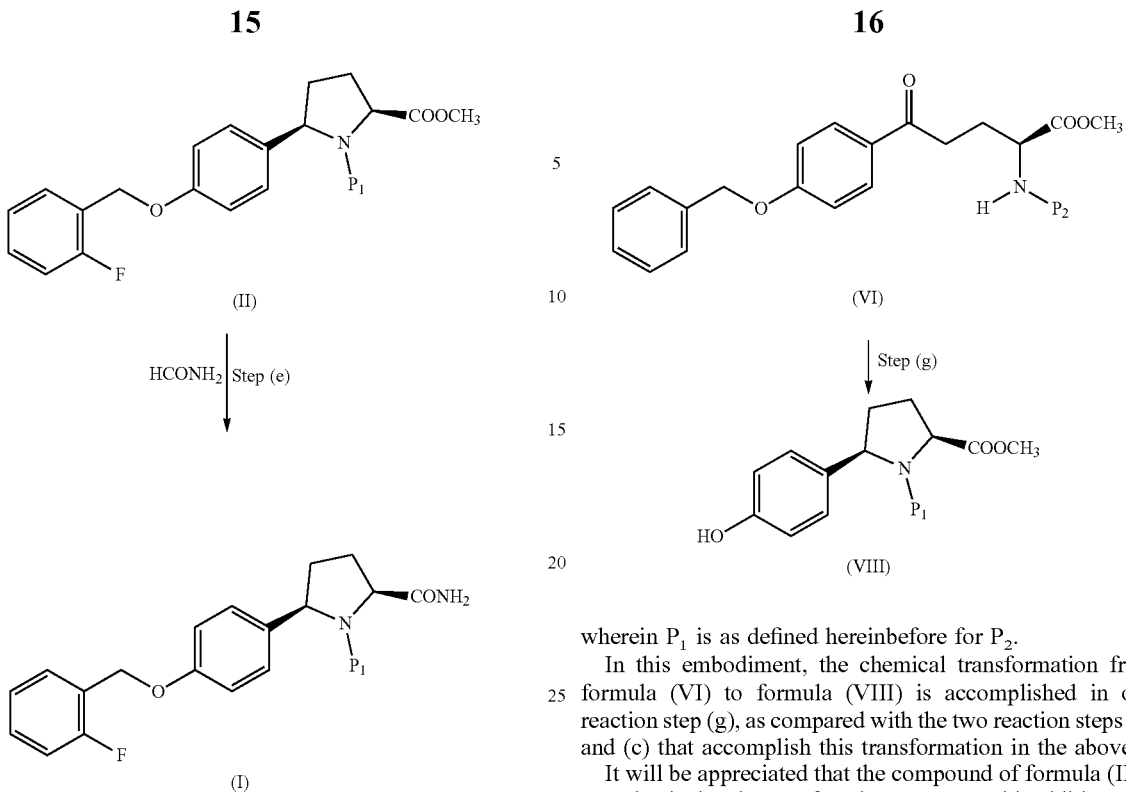

wherein $P^1$ is as defined hereinbefore for $P_2$; followed by
(vi) preparing a compound of formula (III) by deprotecting a compound of formula (I):

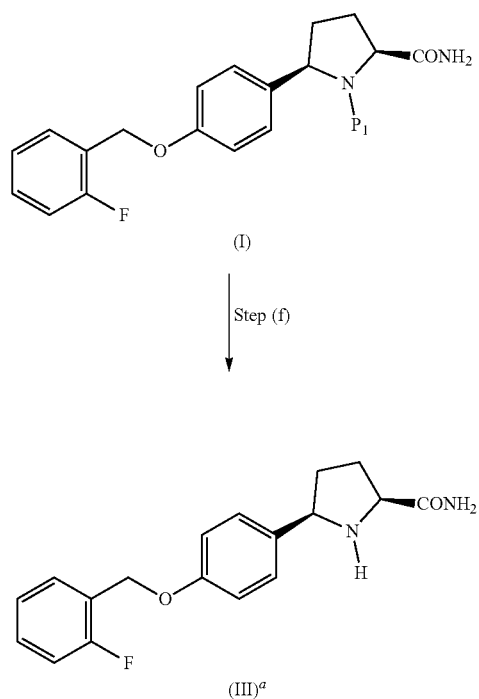

wherein $P^1$ is as defined hereinbefore for $P_2$.

According to another aspect of the invention, there is provided a process for preparing a compound of formula (VIII) from a compound of formula (VI):

wherein $P_1$ is as defined hereinbefore for $P_2$.

In this embodiment, the chemical transformation from formula (VI) to formula (VIII) is accomplished in one reaction step (g), as compared with the two reaction steps (b) and (c) that accomplish this transformation in the above.

It will be appreciated that the compound of formula (III)$^a$ may be isolated as a free base or an acid addition salt depending on the reaction conditions.

Step (a)

In one embodiment of any of the aforementioned processes, $P_2$ represents any suitable amine protecting group as described herein. In a further embodiment, $P_2$ represents tert-butyloxycarbonyl (BOC).

In one embodiment of any of the aforementioned processes, $L_1$ represents a halogen atom. In a further embodiment of any of the aforementioned processes, $L_1$ represents bromine.

In one embodiment of any of the aforementioned processes, step (a) comprises the use of magnesium and a suitable solvent, such as tetrahydrofuran (THF). Examples of exemplary experimental procedure for step (a) as referred to herein are provided as Descriptions 1a, 1b, 1e and 1f-1j.

In an alternative embodiment of any of the aforementioned processes, step (a) comprises the use of isopropyl magnesium chloride (i-PrMgCl) and a suitable solvent, such as tetrahydrofuran (THF) in addition to an n-butyllithium (n-BuLi)-hexane solution. An exemplary experimental procedure for step (a) as referred to herein is provided as Description 1c.

In an alternative embodiment of any of the aforementioned processes, step (a) comprises the use of an isopropyl magnesium chloride (i-PrMgCl)-lithium chloride complex and a suitable solvent, such as tetrahydrofuran (THF) in addition to bis(dimethylamino)ethyl ether. An exemplary experimental procedure for step (a) as referred to herein is provided as Description 1d.

In one embodiment of any of the aforementioned processes, step (a) is conducted via a single step or batch process. Examples of suitable single step or batch processes are described herein in Descriptions 1a, 1b, 1c and 1d and include Grignard, Magnesium "ate" and Turbo Grignard procedures. In one embodiment, the single step or batch process comprises a Grignard procedure (as described in Descriptions 1a and 1b). In an alternative embodiment, the single step or batch process comprises a Magnesium "ate"

procedure (as described in Description 1c). In an alternative embodiment, the single step or batch process comprises a Turbo Grignard procedure (as described in Description 1d).

In one embodiment of any of the aforementioned processes, step (a) is conducted via a continuous or flow process. Examples of suitable continuous or flow processes are described herein in Descriptions 1e and 1f and include an Intermittent Continuous Stirred Tank Reactor and a Plug Flow Reactor. In one embodiment, the continuous or flow process comprises an Intermittent Continuous Stirred Tank Reactor (as described in Description 1e). In an alternative embodiment, the continuous or flow process comprises a Plug Flow Reactor (as described in Descriptions 1f, 1i and 1j).

In one embodiment of any of the aforementioned processes, $L_1$ represents magnesium bromide (as described in Descriptions 1f-1j).

Step (b)

In one embodiment of any of the aforementioned processes, $P_2$ represents any suitable amine protecting group as described herein. In a further embodiment, $P_2$ represents tert-butyloxycarbonyl (BOC).

In one embodiment of any of the aforementioned processes, when $P_2$ represents tert-butyloxycarbonyl (BOC), step (b) comprises the use of a suitable solvent, such as dichloromethane (DCM), acetonitrile or toluene, in particular toluene, and a suitable acid, such as trifluoroacetic acid (TFA), sulfuric acid or methanesulfonic acid. In a further embodiment of any of the aforementioned processes, when $P_2$ represents tert-butyloxycarbonyl (BOC), step (b) comprises the use of trifluoroacetic acid in toluene or methanesulfonic acid in acetonitrile.

In a yet further embodiment of any of the aforementioned processes, when $P_2$ represents tert-butyloxycarbonyl (BOC), step (b) comprises the use of methanesulfonic acid in acetonitrile.

In one embodiment of any of the aforementioned processes, when $P_2$ represents tert-butyloxycarbonyl (BOC), step (b) comprises the use of sulfuric acid in acetonitrile. In another embodiment of any of the aforementioned processes, when $P_2$ represents tert-butyloxycarbonyl (BOC), step (b) comprises the use of methanesulfonic acid in 1:1 (v/v) THF-PhMe (as described in Descriptions 2d and 2e).

In one embodiment of any of the aforementioned processes, step (b) is conducted via a flow chemistry procedure. Examples of exemplary suitable flow chemistry procedures are described herein in Descriptions 2c-2e.

Exemplary experimental procedures for step (b) as referred to herein are provided as Descriptions 2a-2g.

Step (c)

In one embodiment of any of the aforementioned processes, when $P^1$ represents tert-butyloxycarbonyl (BOC), step (c) comprises the use of Boc$_2$O in a suitable solvent, such as methanol and in the presence of a suitable catalyst, such as Pd(OH)$_2$/C, in particular 10-20% Pd(OH)$_2$/C, such as 20% Pd(OH)$_2$/C. Step (c) is typically performed under a hydrogen atmosphere. Exemplary experimental procedures for step (c) as referred to herein are provided as Description 3a-3d.

In one embodiment of any of the aforementioned processes, step (c) is conducted via a flow chemistry procedure comprising the use of Boc$_2$O in a suitable solvent, such as methanol and in the presence of a suitable catalyst, such as Pd/Al$_2$O$_3$, for example 3% Pd/Al$_2$O$_3$. Step (c) is typically performed under a hydrogen atmosphere. Exemplary suitable flow chemistry procedures are described herein in Description 3d.

Step (d)

In one embodiment of any of the aforementioned processes, $L_2$ represents a halogen atom. In a further embodiment of any of the aforementioned processes, $L_2$ represents chlorine or bromine. In a further embodiment of any of the aforementioned processes, $L_2$ represents chlorine. In a further embodiment of any of the aforementioned processes, $L_2$ represents bromine.

In one embodiment of any of the aforementioned processes, when $L_2$ represents bromine, step (d) comprises the use of a suitable base, such as potassium carbonate and a suitable solvent, such as acetonitrile. An exemplary experimental procedure for step (d) as referred to herein is provided as Description 4a.

In one embodiment of any of the aforementioned processes, when $L_2$ represents bromine, step (d) comprises the use of a suitable base, such as NaOMe and a suitable solvent, such as DMF. Exemplary experimental procedures for step (d) as referred to herein are provided as Descriptions 4b-4c and 4h-4i.

In one embodiment of any of the aforementioned processes, when $L_2$ represents chlorine, step (d) comprises the use of a suitable base, such as NaOMe and a suitable solvent, such as DMF. An exemplary experimental procedure for step (d) as referred to herein is provided as Description 4d.

In one embodiment of any of the aforementioned processes, when $L_2$ represents chlorine, step (d) comprises the use of a suitable base, such as NaOMe and a suitable solvent, such as DMSO. An exemplary experimental procedure for step (d) as referred to herein is provided as Description 4e.

In one embodiment of any of the aforementioned processes, when $L_2$ represents bromine, step (d) comprises the use of a suitable base, such as t-BuOK and a suitable solvent system, such as a mixture of ACN and formamide. An exemplary experimental procedure for step (d) as referred to herein is provided as Description 4f.

In one embodiment of any of the aforementioned processes, when $L_2$ represents bromine, step (d) comprises the use of a suitable base, such as t-BuONa and a suitable solvent system, such as a mixture of ACN and formamide. An exemplary experimental procedure for step (d) as referred to herein is provided as Description 4g.

Step (e)

In one embodiment of any of the aforementioned processes, when $L_2$ represents bromine, step (e) comprises the use of a suitable base, such as potassium carbonate and formamide. An exemplary experimental procedure for step (e) as referred to herein is provided as Description 4a.

In one embodiment of any of the aforementioned processes, when $L_2$ represents bromine, step (e) comprises the use of a suitable base, such as NaOMe and a suitable solvent, such as DMF in addition to formamide. Exemplary experimental procedures for step (e) as referred to herein are provided as Descriptions 4b-4c and 4h-4i.

In one embodiment of any of the aforementioned processes, when $L_2$ represents chlorine, step (e) comprises the use of a suitable base, such as NaOMe and a suitable solvent, such as DMF in addition to formamide. An exemplary experimental procedure for step (e) as referred to herein is provided as Description 4d.

In one embodiment of any of the aforementioned processes, when $L_2$ represents chlorine, step (e) comprises the use of a suitable base, such as NaOMe and a suitable solvent, such as DMSO in addition to formamide. An exemplary experimental procedure for step (e) as referred to herein is provided as Description 4e.

In one embodiment of any of the aforementioned processes, when $L_2$ represents bromine, step (d) comprises the use of a suitable base, such as t-BuOK and a suitable solvent system, such as a mixture of ACN and formamide. An exemplary experimental procedure for step (d) as referred to herein is provided as Description 4f.

In one embodiment of any of the aforementioned processes, when $L_2$ represents bromine, step (d) comprises the use of a suitable base, such as t-BuONa and a suitable solvent system, such as a mixture of ACN and formamide. An exemplary experimental procedure for step (d) as referred to herein is provided as Description 4g.

Step (f)

In one embodiment of any of the aforementioned processes, $P_1$ represents any suitable amine protecting group as described herein. In a further embodiment, $P_1$ represents tert-butyloxycarbonyl (BOC).

In one embodiment of any of the aforementioned processes, when $P_1$ represents tert-butyloxycarbonyl (BOC), step (f) comprises the use of a suitable solvent, such as dichloromethane (DCM), acetonitrile, 2-propanol or toluene, in particular toluene, and a suitable acid, such as trifluoroacetic acid (TFA) or methanesulfonic acid or HCl. In a further embodiment of any of the aforementioned processes, when $P_1$ represents tert-butyloxycarbonyl (BOC), step (f) comprises the use of trifluoroacetic acid in toluene or methanesulfonic acid in acetonitrile or HCl in 2-propanol (HCl salt isolated).

In a yet further embodiment of any of the aforementioned processes, when $P_1$ represents tert-butyloxycarbonyl (BOC), step (f) comprises the use of methanesulfonic acid in acetonitrile.

In a yet further embodiment of any of the aforementioned processes, when $P_1$ represents tert-butyloxycarbonyl (BOC), step (f) comprises the use of HCl in 2-propanol (HCl salt isolated).

Exemplary experimental procedures for step (f) as referred to herein is provided as Descriptions 5a-5e.

In one embodiment of any of the aforementioned processes, said process additionally comprises the step of preparing a salt of a compound of formula (III)$^a$ by treating the compound of formula (III)$^a$ with a suitable acid.

In a further embodiment, the salt of a compound of formula (III)$^a$ is the hydrochloride salt and the suitable acid comprises strong hydrochloric acid, such as 4M hydrochloric acid in a suitable solvent, such as 1,4-dioxane.

In an alternative embodiment, the salt of a compound of formula (III)$^a$ is the hydrochloride salt and the suitable acid comprises strong hydrochloric acid, such as hydrochloric acid in a suitable solvent, such as ethanol.

In an alternative embodiment, the salt of a compound of formula (III)$^a$ is the hydrochloride salt and the suitable acid comprises strong hydrochloric acid, such as 1 eq 6N hydrochloric acid in a suitable solvent, such as aqueous 2-propanol.

Step (g)

In one embodiment of any of the aforementioned processes, $P_1$ represents any suitable amine protecting group as described herein. In a further embodiment, $P_1$ represents tert-butyloxycarbonyl (BOC).

In one embodiment of any of the aforementioned processes, when $P_2$ represents benzyloxycarbonyl, step (g) comprises the use $Boc_2O$ in a suitable solvent, such as methanol and in the presence of a suitable catalyst, such as $Pd(OH)_2/C$, in particular 10-20% $Pd(OH)_2/C$. Step (g) is typically performed under a hydrogen atmosphere. Exemplary experimental procedures for step (g) as referred to herein are provided as Descriptions 6a and 6b.

Examples

The invention is illustrated by the Examples described below. The following examples are included merely for purposes of illustration of certain aspects and embodiments of the present invention, and are not intended to limit the invention.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

The following abbreviations are used herein:
ACN Acetonitrile
Boc tert-Butyloxycarbonyl
$Boc_2O$ Di-tert-butyl dicarbonate
n-BuLi n-butyl lithium
t-BuOK potassium tert-butoxide
t-BuONa sodium tert-butoxide
DCM Dichloromethane
DIBAL-H diisobutylaluminum hydride
DMF N,N-dimethylformamide
DMSO Dimethylsulfoxide
HCl Hydrochloric Acid
$HCONH_2$ formamide
$H_2SO_4$ sulfuric acid
$K_2CO_3$ Potassium carbonate
LiCl lithium chloride
Mg magnesium
MTBE Methyl t-butyl ether
MeOH Methanol
MsOH methanesulfonic acid
NaOMe sodium methoxide
$NH_4Cl$ ammonium chloride
$NH_4OH$ ammonium hydroxide
$Pd(OH)_2/C$ palladium(II) hydroxide on carbon (Pearlman's catalyst)
i-PrMgCl isopropylmagnesium chloride
i-PrMgCl—LiCl isopropylmagnesium chloride-lithium chloride complex
TFA Trifluoroacetic acid
THF Tetrahydrofuran Description 1a: Methyl (S)-5-(4-(benzyloxy)phenyl)-2-((tert-butoxycarbonyl)amino)-5-oxopentanoate (D1a) (Batch Process Using Grignard Procedure)

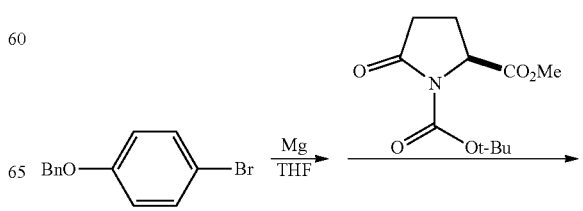

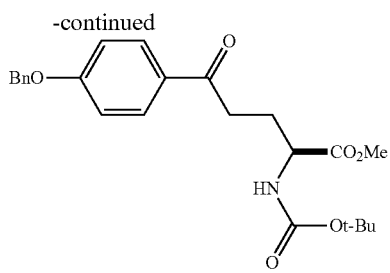

A reactor was charged with THF (350 kg) and the solvent was degassed by nitrogen sparging for about 30 min at 20-30° C. To the degassed THF was charged 1-(benzyloxy)-4-bromobenzene (137 kg (1.78 equiv)). The solids were dissolved at 20-30° C. with agitation and under an inert atmosphere of nitrogen.

A reactor was charged with Mg (21.3 kg (3.0 equiv)) and THF (131 kg) and the mixture was degassed by nitrogen sparging for about 30 min at 20-30° C. To this mixture was added ~5% of the 1-(benzyloxy)-4-bromobenzene-THF solution followed by heating to 50-60° C. under an inert atmosphere of nitrogen. With good agitation, DIBAL-H in toluene (1M; 2.5 kg (0.01 equiv)) was added followed by heating the mixture to 60-70° C. and aging for about 1 h. The remaining amount of the 1-(benzyloxy)-4-bromobenzene-THF solution was added followed by a THF rinse (36 kg) of the reactor. The mixture was aged for about 1 h at 60-70° C. and was cooled to 20-30° C. under an inert atmosphere of nitrogen.

A reactor was charged with THF (382 kg) and the solvent was degassed by nitrogen sparging for about 30 min at 20-30° C. To the degassed THF was charged 1-(tert-butyl) 2-methyl (S)-5-oxopyrrolidine 1,2-dicarboxylate (71 kg (1.0 equiv)), and the resulting solution was cooled to −60 to −70° C. under an inert atmosphere of nitrogen. To this solution was added the Grignard solution while maintaining a reaction temperature of <−60° C. The reactor that contained the Grignard solution was rinsed with THF (61 kg) and the reaction was aged at −60 to −70° C. for about 1 h. The progress of the reaction was monitored (HPLC).

Upon completion, 2-propanol (56 kg) was added while maintaining a reaction temperature of −60 to −70° C., and the reaction was aged for about 30 min. Water (296 kg) was added while maintaining a reaction temperature of <10° C.; the contents of the reactor were warmed to 20-30° C. following the addition. The pH of the mixture was adjusted to 6-7 by addition of 51 wt % acetic acid in water (70 kg). MTBE (220 kg) was added and the mixture was agitated for about 30 min. The layers were separated, the organic layer was clarified by filtration and was concentrated to about 3-4V. MTBE (220 kg) was added and the resulting solution was concentrated to about 3-4V. MTBE (150 kg) was added and the resulting solution was heated to 35-45° C. n-Heptane (250 kg) was added slowly while maintaining a reaction temperature of 35-45° C., the mixture was aged for 1-2 h, cooled to 0-5° C. and aged for 3-5 h. The solids were isolated by filtration, washed with n-heptane (74 kg) and dried in vacuo at 50-60° C. to constant weight to afford 96.7 kg (77.5%) of the title compound.

Description 1b: Methyl (S)-5-(4-(benzyloxy)phenyl)-2-((tert-butoxycarbonyl)amino)-5-oxopentanoate (D1b) (Batch Process Using Grignard Procedure) (Alternative Procedure)

A reactor was charged with degassed THF (1090 kg) and 1-(benzyloxy)-4-bromobenzene (329 kg (1.46 equiv)). The solids were dissolved at 20-25° C. with agitation and under an inert atmosphere of nitrogen.

A reactor was charged with Mg turnings (31.9 kg (1.53 equiv)) and degassed THF (389 kg) under an inert atmosphere of nitrogen. To this mixture was added ~5% of the 1-(benzyloxy)-4-bromobenzene-THF solution (~70 kg) followed by heating to 50-60° C. With good agitation, DIBAL-H in toluene (1.5M; 4.55 kg (0.0093 equiv)) was added followed by addition of toluene (2.16 kg) into the reactor through the charging line. The mixture was heated to 60-70° C. and aged for about 1 h. The remaining amount of the 1-(benzyloxy)-4-bromobenzene-THF solution was added followed by a degassed THF rinse (51 kg) of the reactor. The mixture was aged for about 1 h at 60-70° C. and was cooled to 20-30° C. under an inert atmosphere of nitrogen.

A reactor was charged with degassed THF (1090 kg) and 1-(tert-butyl) 2-methyl (S)-5-oxopyrrolidine 1,2-dicarboxylate (208 kg (1.0 equiv)), and the resulting solution was cooled to −60 to −70° C. under an inert atmosphere of nitrogen. To this solution was added the Grignard solution while maintaining a reaction temperature of <−50° C. The reactor that contained the Grignard solution was rinsed with degassed THF (208 kg) and the reaction was aged at −60 to −70° C. for about 1 h. The progress of the reaction was monitored (HPLC).

Upon completion, 2-propanol (164 kg) was added while maintaining a reaction temperature of <−40° C., and the reaction was aged for 20-30 min. Water (100 kg) was added while maintaining a reaction temperature of <−20° C.; the contents of the reactor were warmed to −10 to −20° C. following the addition. The mixture was transferred into another reactor and water (940 kg) was added while maintaining a reaction temperature of <10° C.; the contents of the reactor were warmed to 20-30° C. following the addition. The pH of the mixture was adjusted to 6.0-7.0 by addition of 50 wt % acetic acid in water (~170 kg). MTBE (647 kg) was added and the mixture was agitated for 20-30 min. The layers were separated, and the organic layer was stirred for 20-30 min with a brine solution prepared from NaCl (48 kg) and water (390 kg). The layers were separated, the organic layer was clarified by filtration and the filtration apparatus was washed with THF (30 kg). The solution was concentrated to about 5.5-6× the input mass of 1-(tert-butyl) 2-methyl (S)-5-oxopyrrolidine 1,2-dicarboxylate at a temperature of 45-50° C. MTBE (647 kg) was added and the resulting solution was concentrated to about 5.5-6× the input mass of 1-(tert-butyl) 2-methyl (S)-5-oxopyrrolidine 1,2-dicarboxylate at a temperature of 45-50° C. MTBE (661 kg) was added and the resulting solution was concentrated to about 5.5-6× the input mass of 1-(tert-butyl) 2-methyl (S)-5-oxopyrrolidine 1,2-dicarboxylate at a temperature of 45-50° C. MTBE (77 kg) was added, the solution was sampled and analysed for residual THF content (if the result was >15%, MTBE (661 kg) was added and the solution was concentrated at 45-50° C. to about 5.5-6× the input mass of 1-(tert-butyl) 2-methyl (S)-5-oxopyrrolidine 1,2-dicarboxylate). The solution was cooled to 35-45° C. and n-Heptane (726 kg) was added slowly while maintaining a reaction temperature of 35-45° C. The mixture was aged for 1-2 h, cooled to 15-25° C. over 2-3 h, cooled to 0-5° C. and aged for 3-5 h. The solids were isolated by centrifugation and washed with n-heptane (214 kg). The wet solids (~328 kg) were dissolved in THF (683 kg) at 40-50° C. The solution was cooled to 35-45° C. and n-heptane (564 kg) was added slowly while maintaining a reaction temperature of 35-45° C. The mixture was aged for 1-2 h, cooled to 15-25° C. over 2-3 h, cooled to 0-5° C. and aged for 3-5 h. The solids were isolated by centrifugation, washed with n-heptane (167 kg) and dried in vacuo at 50-60° C. to constant weight to afford 252 kg (69%) of the title compound.

Description 1c: Methyl (S)-5-(4-(benzyloxy)phenyl)-2-((tert-butoxycarbonyl)amino)-5-oxopentanoate (D1c) (Batch Process Using Magnesium "Ate" Procedure)

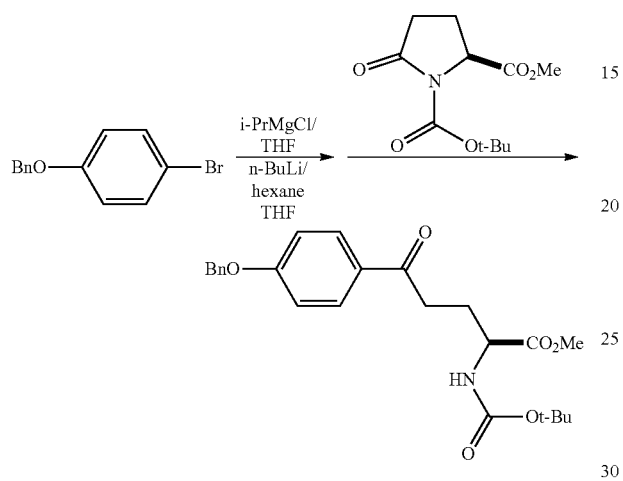

A reactor was charged with THF (249 kg) and the solvent was degassed by nitrogen sparging for about 30 min at 20-30° C. To the degassed THF was charged 1-(tert-butyl) 2-methyl (S)-5-oxopyrrolidine 1,2-dicarboxylate (71 kg (1.0 equiv)), and the resulting solution was stirred at 20 to 30° C. under an inert atmosphere of nitrogen.

A reactor was charged with THF (460 kg) and the mixture was degassed by nitrogen sparging for about 30 min at 20-30° C. To the degassed THF was charged 1-(benzyloxy)-4-bromobenzene (93 kg (1.2 equiv)) and the solution was degassed in triplicate. The solution was cooled to −40 to −50° C. under an inert atmosphere of nitrogen. To this solution was added i-PrMgCl-THF solution (51.3 kg, 2M; 0.36 equiv) while maintaining a reaction temperature of <−40° C. To this solution was added n-BuLi-hexane solution (71.3 kg, 2.5M; 0.90 equiv) while maintaining a reaction temperature of <−40° C. The contents of the reactor were aged at −40 to −50° C. for 1-1.5 h. The solution was cooled to −60 to −70° C. under an inert atmosphere of nitrogen.

The 1-(tert-butyl) 2-methyl (S)-5-oxopyrrolidine 1,2-dicarboxylate-THF solution was added to the reactor containing the organomagnesium "ate" solution while maintaining a reaction temperature of −60 to −70° C.; the contents of the reactor were aged for about 1 h. The progress of the reaction was monitored (HPLC).

Upon completion, 10% NH$_4$Cl solution (389 kg) was added while maintaining a reaction temperature of <−40° C. Following the addition, the contents of the reactor were warmed to 20-30° C. The pH of the mixture was adjusted to 6-7 by addition of 50 wt % acetic acid in water (24.4 kg). n-Heptane (97 kg) was added and the mixture was agitated for 20-30 min at 20–30° C. The layers were separated and the organic layer was concentrated in vacuo to about 270 L at <50° C. The contents of the reactor were cooled to 20-30° C. and n-heptane (490 kg) was added followed by slurry aging for 2-3 h. The slurry was cooled to 0-5° C. and aged for 2-3 h. The solids were isolated by filtration, washed with a solution composed of n-heptane (58 kg) and THF (25 kg) and were dried in vacuo at 50-60° C. to constant weight to afford 102.95 kg (82.5%) of the title compound.

A reactor was charged with the title compound (102.95 kg) and THF (469 kg). The contents of the reactor were warmed to 40-50° C., aged for 1-2 h, cooled to 20-30° C. and concentrated to a volume of about 250 L. n-Heptane (490 kg) was added and the mixture was agitated for 2-3 h at 20-30° C. The mixture was cooled to 0-5° C. and aged for 2-3 h. The solids were isolated by filtration, washed with n-heptane (213 kg) and dried in vacuo at 50-60° C. to constant weight to afford 87.95 kg (70.5%) of the title compound.

Description 1d: Methyl (S)-5-(4-(benzyloxy)phenyl)-2-((tert-butoxycarbonyl)amino)-5-oxopentanoate (D1D) (Batch Process Using Turbo Grignard Procedure)

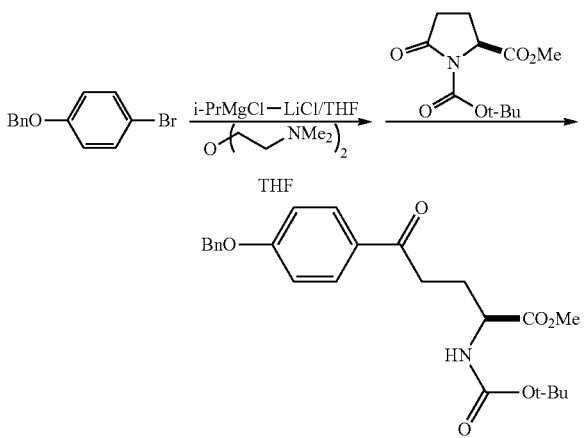

A clean 100 mL EasyMax reactor was swept with dry nitrogen, the flow was reduced and i-PrMgCl—LiCl complex in THF (41.7 g, 1.3M, 1.0 eq) was added to the reactor and the temperature was set to 20° C. Bis(dimethylamino)ethyl ether (9.13 g, 1.0 eq) was added in a single portion, the mixture was stirred for 5 min, and 4-benzyloxybromobenzene (15.0 g, 1.0 eq) was added in a single portion. The reaction was heated to 40° C. under an inert atmosphere of nitrogen and held at this temperature until full conversion was observed (ca. 3.5 h).

A clean 100 mL EasyMax reactor was swept with dry nitrogen, the flow was reduced and dry THF (45 mL). 1-(tert-butyl) 2-methyl (S)-5-oxopyrrolidine 1,2-dicarboxylate (5.0 g, 1.0 eq) was charged in a single portion and the solution was cooled to −35° C. under an inert atmosphere of nitrogen. The Grignard solution (26.4 mL, 0.85M, 1.1 eq) was then added at a rate of 0.5 mL/min while maintaining a reaction temperature of <−30° C. The progress of the reaction was monitored (HPLC). Upon completion the reaction was neutralized by the addition of a 14.6 wt % AcOH/water solution (24 mL). The reaction was then warmed to −10° C., then to 0° C. A 20% aqueous NH$_4$Cl solution (10.3 g) was added followed by a pH adjustment with 1M HCl (14 mL), then with 6M HCl to an endpoint of pH 1. The reaction mixture was transferred to a separatory funnel with the aid of 25 ml of THF. The phases were separated and the organic layer washed with saturated aqueous NaCl solution (16 g).

The organic layer was concentrated under reduced pressure at <50° C. to afford a crude product solution (19.4 g).

The crude product solution was transferred to a clean 100 mL EasyMax reactor and was heated to 35° C. Heptane (20 mL) was then added over about 30 sec. The mixture was cooled to 10° C. and held for about 30 min. The solids were filtered, washed twice with 2:1 heptane/MTBE mixture (14 mL) and dried to constant weight to afford 4.147 g (47%) of the title compound.

Description 1e: Methyl (S)-5-(4-(benzyloxy)phenyl)-2-((tert-butoxycarbonyl)amino)-5-oxopentanoate (D1E) (Flow Process Using Intermittent Continuous Stirred Tank Reactor)

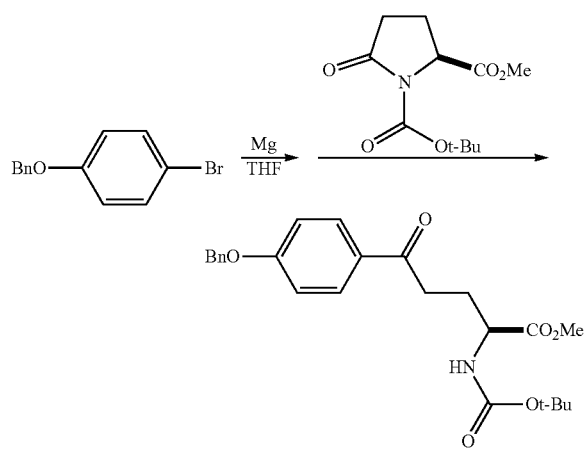

Reactor 1 was charged with 1-(benzyloxy)-4-bromobenzene (145 g (1.0 eq)) and the reactor was flushed with nitrogen. THF (490 g) was added and solids were dissolved at 20-30° C. by agitation; the solution was kept under an inert atmosphere of nitrogen.

Reactor 2 was charged with Mg (13.66 g (1.02 eq relative to reactor 1 charge)) and the reactor was flushed with nitrogen. Iodine (0.14 g (0.001 eq relative to the 1-(benzyloxy)-4-bromobenzene charge)) was charged followed by addition of 5% of the prepared 1-(benzyloxy)-4-bromobenzene-THF solution. The contents of the reactor were warmed to 50-65° C. and after color dissipation, the remainder of the prepared 1-(benzyloxy)-4-bromobenzene-THF solution (Reactor 1) was added while maintaining a reaction temperature of 50-70° C. The contents of the reactor were stirred at 60-70° C. for about 1 h, cooled to 20-30° C. and held under an inert atmosphere of nitrogen.

Grignard Solution Batch 1

Reactor 3 was charged with 1-(benzyloxy)-4-bromobenzene (2.755 kg (1.0 eq)) and the reactor was flushed with nitrogen. THF (9.29 kg) was added and solids were dissolved at 20-30° C. by gentle agitation; the solution was kept under an inert atmosphere of nitrogen. Reactor 4 was charged with Mg (259.2 g (1.02 eq relative to the reactor 3 charge)) and the reactor was flushed with nitrogen. The contents of Reactor 2 were charged and the mixture was warmed to 50-65° C. The prepared 1-(benzyloxy)-4-bromobenzene-THF solution in Reactor 3 was added while maintaining a reaction temperature of 50-70° C. The contents of the reactor were stirred at 60-70° C. for about 1 h and cooled to 20-30° C. About 95% of this Grignard solution was transferred into Reactor 5 and held under an inert atmosphere of nitrogen. A sample was pulled from Reactor 5 for analysis (residual 1-(benzyloxy)-4-bromobenzene (HPLC); Grignard reagent concentration). The remaining 5% of this Grignard solution was held in Reactor 4 under an inert atmosphere of nitrogen.

Grignard Solution Batch 2

Reactor 3 was charged with 1-(benzyloxy)-4-bromobenzene (2.90 kg (1.0 eq)) and the reactor was flushed with nitrogen. THF (9.78 kg) was added and solids were dissolved at 20-30° C. by gentle agitation; the solution was kept under an inert atmosphere of nitrogen. Reactor 4 was charged with Mg (273.1 g (1.02 eq relative to the reactor 3 charge)) and the mixture was warmed to 50-65° C. The prepared 1-(benzyloxy)-4-bromobenzene-THF solution in Reactor 3 was added while maintaining a reaction temperature of 50-70° C. The contents of the reactor were stirred at 60-70° C. for about 1 h and cooled to 20-30° C. About 95% of this Grignard solution was transferred into Reactor 6 and held under an inert atmosphere of nitrogen. A sample was pulled from Reactor 6 for analysis (residual 1-(benzyloxy)-4-bromobenzene (HPLC); Grignard reagent concentration). The remaining 5% of this Grignard solution was held in Reactor 4 under an inert atmosphere of nitrogen.

Grignard Solution Batch 3

Reactor 3 was charged with 1-(benzyloxy)-4-bromobenzene (2.90 kg (1.0 eq)) and the reactor was flushed with nitrogen. THF (9.78 kg) was added and solids were dissolved at 20-30° C. by gentle agitation; the solution was kept under an inert atmosphere of nitrogen. Reactor 4 was charged with Mg (273.2 g (1.02 eq relative to the reactor 3 charge)) and the mixture was warmed to 50-65° C. The prepared 1-(benzyloxy)-4-bromobenzene-THF solution in Reactor 3 was added while maintaining a reaction temperature of 50-70° C. The contents of the reactor were stirred at 60-70° C. for about 1 h, cooled to 20-30° C. and held under an inert atmosphere of nitrogen. A sample was pulled for analysis (residual 1-(benzyloxy)-4-bromobenzene (HPLC); Grignard reagent concentration).

Reaction of Grignard Reagent with 1-(tert-butyl) 2-methyl (S)-5-oxopyrrolidine 1,2-dicarboxylate The reaction was performed in 12 cycles; a representative cycle is described below. In total, 6.46 kg of 1-(tert-butyl) 2-methyl (S)-5-oxopyrrolidine 1,2-dicarboxylate was processed forward to the title compound.

Reactor 7 was charged with 1-(tert-butyl) 2-methyl (S)-5-oxopyrrolidine 1,2-dicarboxylate (2.21 kg) and THF (5.89 kg) and the solids were dissolved at 20-30° C. by gentle agitation under an inert atmosphere of nitrogen.

Reactor 8 was charged with THF (0.98 kg) and the solvent was cooled to about −10° C. under an inert atmosphere of nitrogen. Solutions of the Grignard reagent (3.2 kg) in Reactor 6 and the 1-(tert-butyl) 2-methyl (S)-5-oxopyrrolidine 1,2-dicarboxylate-THF solution (2.0 kg) in Reactor 7 were simultaneously pumped into Reactor 8 over 15 min while maintaining a reaction temperature of <30° C. The contents of Reactor 8 were stirred for an additional 15 min; the final reaction temperature was 0-10° C. The contents of Reactor 8 were transferred to Reactor 9, cooled to about −5° C. and the reaction was quenched by addition of 1M aqueous $H_2SO_4$ solution (1.20 equiv) while maintaining a reaction temperature of ≤10° C. The mixture was stirred for 30 min, was transferred to Reactor 10 and was heated to 25-30° C. The mixture was transferred to Reactor 11, toluene (2.39 kg) was charged and the mixture was agitated. The mixture was transferred to Settler 1 and the organic layer was transferred to Reactor 12 using a metering pump. Water (1.65 kg) wash charged to Reactor 12, the mixture was agitated, transferred to Settler 2 and the organic layer was transferred to a storage container using a metering pump.

Product Isolation

The contents of the storage container (organic streams from 12 reaction cycles) was concentrated in Reactor 13 to an endpoint of 65° C. (pot temperature) at 200 torr. The contents of the reactor were cooled to 30° C., then to 0 to −10° C. and aged for 0.5-2 h. The solids were isolated by filtration, washed with toluene (7.50 kg) and dried in vacuo at 50° C. and <10 torr to give 8.76 kg (77%) of the title compound.

Description 1f: Methyl (S)-5-(4-(benzyloxy)phenyl)-2-((tert-butoxycarbonyl)amino)-5-oxopentanoate (D1f) (Flow Process Using Plug Flow Reactor)

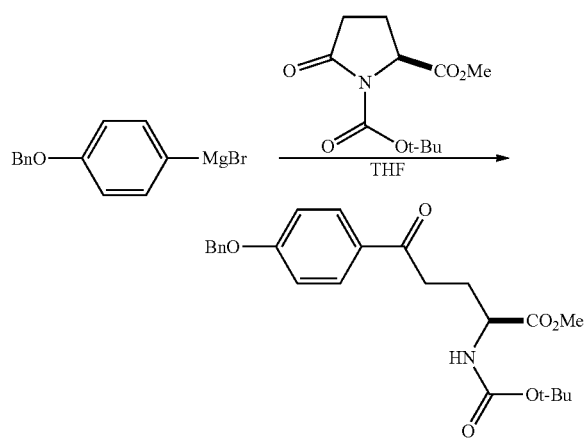

A flow reactor with two reagent inputs, ⅜ inch tubing for reagent transfer, and two ½ inch jacketed static mixers connected in series (35 mL volume) was assembled. Gear pumps were used to transfer reagents to the flow reactor. Mass flow meters were used to measure the flow rates of the reagents. Thermocouples were placed to monitor the temperature of the (4-benzyloxy)phenylmagnesium bromide (Grignard) and 1-(tert-butyl) 2-methyl (S)-5-oxopyrrolidine 1,2-dicarboxylate solutions prior to entering the tube-in-tube mixer T, as well as the out-flowing reaction stream from the static mixers. A fourth thermocouple measured the temperature of the collection vessel. A peristaltic pump was used to transfer an aqueous acetic acid quench solution to the reaction stream as it exited from the static mixers. A standard T-mixer was used to join these reaction streams. The quenched reaction mixture flowed through a cooled coil into a jacketed collecting vessel. The approximate residence time through the static mixers was calculated to be ~4.5 seconds.
Solution A: 0.57M (4-benzyloxy)phenylmagnesium bromide (Grignard) solution in THF (1.3 equiv used).
Solution B: 0.44M 1-(tert-butyl) 2-methyl (S)-5-oxopyrrolidine 1,2-dicarboxylate (0.750 kg) in THF (6.5 L)
Solution C: 2.9M glacial acetic acid (517 g) in water (3.013 L) to provide a 2.9 M solution. The quenched reaction mixture flowed into a collecting vessel containing 20% aqueous NH₄Cl (1.465 kg) at 0° C.

The pre-cooling loop for Solution B was set to a bath temperature of −20 to −22° C. The static mixer jacket coolant was set to a temperature of −25° C. The pre-cooling loop for Solution A was set to a jacket temperature of −5° C. The continuous quench tube reactor was set to a bath temperature of 0° C.

After the jacket temperatures and cooling baths were allowed to reach desired temperatures, Solution A was pumped at a rate of ~250 mL/min through the outside tube of the tube-in-tube mixer and met the Solution B that was pumped through the inner tube at a rate of 250 mL/min. Simultaneously to the reagent streams, the flow rate of the 2.9M aqueous acetic acid solution was initiated and set to approximately 130 mL/min. Reagent flow rates were measured with mass flow meters and temperatures were measured with thermocouples.

The reaction was run for about 20 min; a total of 5.663 kg of Solution B, 6.237 kg of Solution A and 3.530 kg of 2.9M aqueous acetic acid solution were charged during the reaction. The lines were rinsed with THF (1.252 kg) immediately after the reaction was finished.

The pH of the aqueous layer in the collection vessel was measured at 6.08. The pH was adjusted to 5.05 with 1N HCl (2.05 kg) followed by the addition of 1V:1V AcOH/water (162 g). The reactor jacket temperature was set to 10° C. and the contents of the reactor were stirred for 12 h. The pH of the mixture was further adjusted to 2.06 by adding 37% HCl (0.301 kg) and the mixture was stirred at 0-10° C. for 15 to 30 min.

The aqueous layer was separated and the organic layer was stirred for 20 min with a 25% brine solution (1.995 kg). The aqueous layer was separated; the organic layer was held at 10° C. overnight. The organic layer was concentrated at 35-40° C. (jacket temperature) and 25-30 mm Hg. Upon reaching a volume of about 9.5 L, a well developed slurry was noted. The concentration was continued to a volume of about 4.5 L. The slurry was warmed to 31° C. and heptane (3.145 kg) was added. The slurry was heated to 35° C., stirred for 30 min, and was cooled to and held at 20 to 22° C. The slurry was cooled to 10° C. and stirred for at least 2 h. Solids were collected by filtration and washed with 2:1 heptane/MTBE (2×1.5 L). The solids were dried to constant weight in vacuo to yield 990 g (86.8%) of the title compound.

Description 1g: methyl (S)-5-(4-(benzyloxy)phenyl)-2-((tert-butoxycarbonyl)amino)-5-oxopentanoate

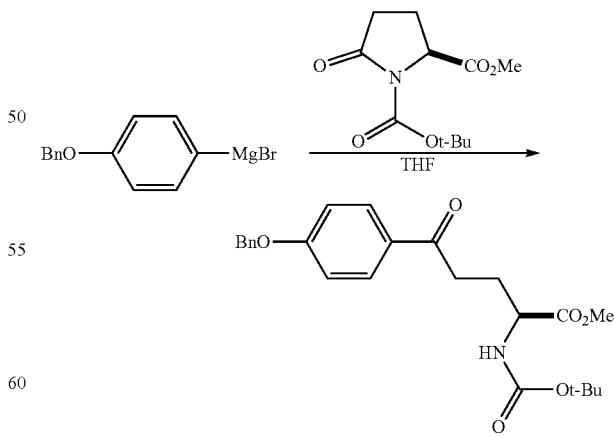

A reactor was charged with degassed THF (1199 kg) and 1-(benzyloxy)-4-bromobenzene (450 kg). The solids were dissolved at 20-25° C. with agitation and under an inert atmosphere of nitrogen. The mixture was heated to reflux for 15 min, then cooled to 20-30° C. A reactor was charged with Mg turnings (43.6 kg) and degassed THF (399 kg) under an inert atmosphere of nitrogen. To this mixture, a solution of DIBAL-H (25% in toluene, 6.2 kg) was added followed by addition of toluene (3.7 L) into the reactor through the charging line. The mixture was heated to reflux for 10-15 minutes followed by charging of 5% of the 1-(benzyloxy)-4-bromobenzene-THF solution. The contents of the reactor were held for 1 h under reflux; reaction initiation was confirmed. The remainder of the 1-(benzyloxy)-4-bromobenzene-THF solution was added over 3-4 h. Following the charge, the temperature was adjusted to 20-30° C.

A reactor was charged with degassed THF (760 kg) and 1-(tert-butyl) 2-methyl (S)-5-oxopyrrolidine 1,2-dicarboxylate (284.9 kg), and the resulting solution was heated to reflux under an inert atmosphere of nitrogen, maintained at reflux for 10-15 min, then cooled to –60° C. to –70° C. To this solution was added the Grignard solution while maintaining a reaction temperature of <–50° C. The reactor which contained the 1-(benzyloxy)-4-bromobenzene-THF solution was rinsed with degassed THF (22 kg) and the rinse was charged into the reaction. The contents of the reactor were aged at –60 to –70° C. for about 1 h. The progress of the reaction was monitored for completion (HPLC).

A reactor was charged with 2-propanol (285 L) and THF (253 kg). With good agitation the reaction was quenched into this THF-2-propanol solution while keeping the temperature between –20° C. and 0° C. The reactor was rinsed forward with THF (53 kg), and the mixture was stirred vigorously for 5-10 min. Water (712 L) was added while maintaining a reaction temperature of <20° C.; the pH of the mixture was adjusted to 6.0-7.0 by addition of 50 wt % acetic acid in water (~170 kg) while controlling the temperature below 20° C. The reaction mixture was warmed to 20-30° C., stirred for 20-30 min and the phases were separated. Sodium chloride (42 kg) and water (255 L) were charged, the mixture was stirred for 55-65 min, and the phases were separated. THF (125 kg) was charged and the solution was concentrated by distillation under vacuum at a temperature of 40-45° C. The distillation was stopped when the weight of the reaction mixture was between 5.5-6.0× the weight of the input mass of 1-(tert-butyl) 2-methyl (S)-5-oxopyrrolidine 1,2-dicarboxylate. The reaction mixture was heated to 35-45° C. Heptane (994 kg) was charged to the reaction mixture, the contents of the reactor were maintained at 35-45° C., aged for 1-2 h, cooled to 15-25° C. over 2-3 h, cooled to 0-5° C. and aged for 3-5 h. The solids were isolated by centrifugation in three portions; each portion was washed with heptane (97 kg) followed by acetonitrile (59 kg) to give 389 kg of wet product. Based on LOD measurements, 375.3 kg (76.6%) of the title compound was obtained.

Description 1h: benzyl (S)-5-(4-(benzyloxy)phenyl)-2-((tert-butoxycarbonyl)amino)-5-oxopentanoate

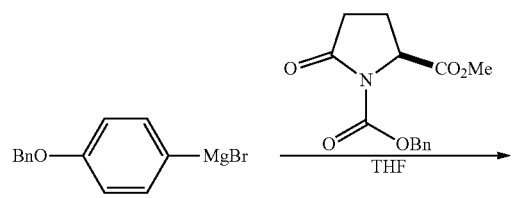

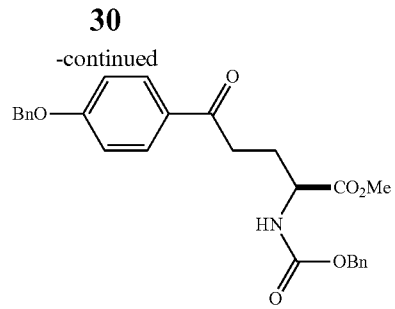

A reactor was charged with 1-benzyl 2-methyl (S)-5-oxopyrrolidine 1,2-dicarboxylate (69.3 g) and anhydrous THF (450 g) and the resulting solution was cooled to about –65° C. under an inert atmosphere of nitrogen. A solution of 0.8M (4-benzyloxy)phenylmagnesium bromide in THF (1.1 eq) was added over about 2 h, and the progress of the reaction was monitored by HPLC. Upon completion, the reaction was quenched by simultaneous addition of 1M sulfuric acid (1.1 eq) and toluene (264 g) over about 30 min. The resulting mixture was warmed from ~10° C. to ambient temperature and was aged for about 30 min. The phases were separated, and the organic layer was washed with 10 wt % brine (180 g) and water (180 g). The organic solution was concentrated to about 6V at about 50° C. and ≤170 mbar (distillate: 650 g/710 mL). The resulting solution was heated to about 65° C. and a solution of toluene (105 g) and methylcyclohexane (200 g) was added dropwise while maintaining a temperature of about 65° C. The solution was cooled to 0-5° C. and aged for about 1 h. The solids were isolated by filtration, washed with cold (0-5° C.) methylcyclohexane (200 g in 6 portions) and dried at 45° C. in vacuo to constant weight to give 76.6 g (66%) of the title compound.

Description 1i: methyl (S)-2-(((benzyloxy)carbonyl)amino)-5-(4-(benzyloxy)phenyl)-5-oxopentanoate—Flow Chemistry Procedure

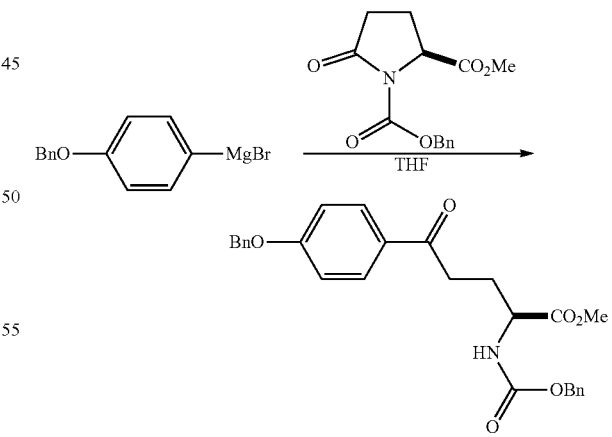

Solution A: 0.8M (4-benzyloxy)phenylmagnesium bromide solution in THF
Solution B: 0.88M 1-benzyl 2-methyl (S)-5-oxopyrrolidine 1,2-dicarboxylate (25.0 g) solution in anhydrous THF
Solution C: 1M aqueous sulfuric acid
Equipment: plug flow reactor with a Y-mixer; 10 mL reaction loop Reaction Conditions:
reagent flow rates:
solution A: 5.27 mL/min (1.3 eq)
solution B: 4.72 mL/min (1.0 eq)
solution C: 5.75 mL/min (1.5 eq)
residence time: 1 min
reaction temperature: 25° C.
collection time: 2 h (theory: 0.36 mol title product)
the quenched reaction mixture flowed into a collecting vessel Following collection of the quenched reaction mixture, the phases were separated and the upper organic layer was concentrated to dryness in vacuo. The solids were dissolved in fresh THF (5.5V) at 45° C. The solution was cooled to −5° C. over about 160 min and was aged overnight. The solids were collected by filtration, washed with heptane (5.5V, total) and dried to constant weight at 55° C. in vacuo to afford 18.61 g (45%) of the title product.

The combined filtrate and wash containing additional solids was transferred to a reactor, cooled to −5° C. over 2 h and aged for an additional 4 h. The solids were collected by filtration, washed with heptane (2×2V) and dried to constant weight at 55° C. in vacuo to afford 11.37 g (27%) of the title product.

Description 1j: methyl (S)-5-(4-(benzyloxy)phenyl)-2-((tert-butoxycarbonyl)amino)-5-oxopentanoate—Flow Chemistry Procedure

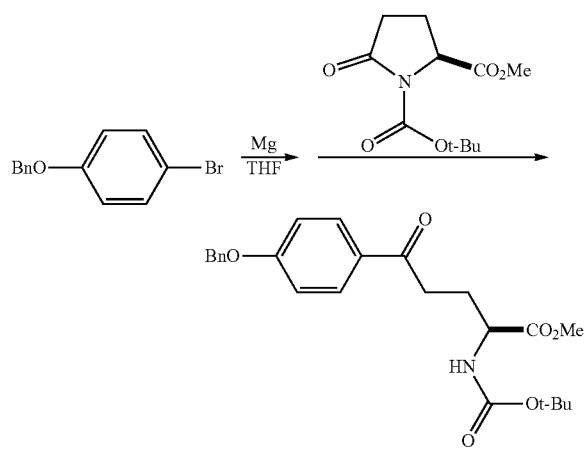

The CSTR flow setup consists of one 1 L stirred tank for reaction, one 1 L settling tank and one 10 L Schlenk type collection vessel. The stirred tank was equipped with a solid addition device, a reflux condenser, and a dip-tube (set to a 500 mL working volume) with an inner transfer line.

Step 1: A stirred tank reactor was pre-charged with THF (70 ml), and magnesium (50.8 g, 5 eq), and stirred at room temperature overnight. The solid addition device was filled with magnesium. The reaction was initiated by adding (4-(benzyloxy)phenyl)magnesium bromide 0.77M solution (7.7 g, 5.9 mmol). The jacket temperature was increased to 55° C. A solution of 1-bromo-4-benzylphenol (0.85 M in THF) was added at a rate of 7.8 ml/min to the stirred reaction vessel. After seven minutes, solid addition of magnesium started at a rate of 0.161 g/min. The total amount of magnesium for the entire run was (175 g, 7.18 mol, 1 equiv)[1] and was calculated to keep 5 eq of magnesium in the stirred tank reactor over the course of the run. When the liquid level in the tank reached the level of the dip tube, a pump activated pulling material to the settling tank at a rate to maintain the 500 mL filling level in the CSTR. The approximate residence time of the solution in the jacketed reactor was 62 minutes. The product was transferred into the settling tank (unstirred), held for another residence time (1 hour), and subsequently transferred to a final collection vessel. The entire process was run for 18 hours.

Step 2: Grignard Addition: The equipment consists of tubular pipe reactor, heat exchanger, and a series of centrifugal phase separators. The tubular reactor accommodates mixing of two reagents for the conversion to methyl (S)-5-(4-(benzyloxy)phenyl)-2-((tert-butoxycarbonyl)amino)-5-oxopentanoate and quenching of the product solution with an acid solution. The centrifugal phase separators separate the product containing organic phase from the waste aqueous phase. The reagent (methyl-N-boc-pyroglutamate, Grignard, and sulfuric acid solutions were transferred continuously at controlled flowrates from their respective storage tank to pass through the tubular pipe reactor, heat exchanger and finally to the centrifugal extractors.

Reaction/Quench/Work-up: The 0.82 M Grignard solution was fed continuously from the storage tank at a flow rate of 32.6 mL/min (1.19 eq), simultaneously a 0.817 M methyl N-boc-pyroglutamate solution stream was fed continuously at 27.4 ml/min through a heat exchanger to pre-cool it to −8° C. The tubular reactor where the reaction between the reagent N-boc-pyroglutamate and Grignard solution occurred was attached to a heat exchange unit with chiller fluid set at 10° C. After passing through the reaction zone, 1.0 M sulfuric acid was introduced at a rate 22.4 ml/min. The residence time of the solution from reagent introduction to acid quench was 8 seconds. From sulfuric acid introduction to phase split the residence time was ca. 80 seconds. The quenched mixture passed through another heat exchanger to increase the temperature to 30° C. for phase split. This material was directly fed into a centrifugal extractor to remove the aqueous component. The obtained organic layer was subsequently mixed with a solution of brine and sodium bicarbonate (14.5 ml/min) in a second centrifugal extractor. The final product containing organic layer was collected into a glass bottle. The process was run for 3.7 hours.

Crystallization: The product-containing organic layer above was transferred to a 10 L reactor for solvent switch to a lower water content THF-Heptane solvent system by vacuum distillation. A total of 6867 mL THF (appx. 9.5% v/v) in Heptane was added to the reactor and subsequently distilled in appx. 2 equal portions maintaining distillation under reduced pressure (appx. 600-700 mbar) at temperature within 60-65° C. to replace the original solvent (water-containing THF).[3] The final solution obtained (appx. 11.5 L) was cooled to 0-5° C. with a cooling rate 0.5 C/min and the resulting slurry was filtered, washed with Heptane and dried under vacuum at 60° C. to obtain 1.765 kg of product.

Description 2a: Methyl (S)-5-(4-(benzyloxy)phenyl)-3,4-dihydro-2H-pyrrole-2-carboxylate (D2a)

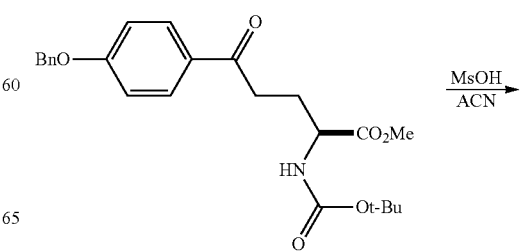

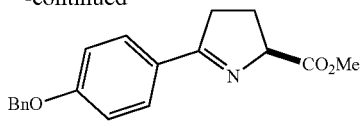

A reactor was charged with methyl (S)-5-(4-(benzyloxy)phenyl)-2-((tert-butoxycarbonyl)amino)-5-oxopentanoate (180 kg) and ACN (486 kg) and the slurry temperature was adjusted to 10-15° C. A solution of methanesulfonic acid (117.5 kg (2.9 eq)) in ACN (75 kg) was added while maintaining a reaction temperature of <25° C. The reaction temperature was adjusted to 22-26° C. and the contents of the reactor were stirred for 1-1.5 h. The progress of the reaction was monitored (HPLC). Upon completion, the contents of the reactor were cooled to 10-15° C. and a solution of 4.0N NH$_4$OH (299 kg) was added to a pH of 7-8 while maintaining a reaction temperature of <25° C. The phases were separated and the upper organic layer was heated to 30-40° C. While maintaining a reaction temperature of 30-40° C., 2-propanol (101 kg) and water (430 kg) were added to the reactor. The solution was cooled to 17-19° C. and was seeded (1.8 kg). The slurry was stirred for 1-2 h at 14-19° C., cooled to 7-12° C., aged for 1-2 h and cooled to 2-7° C. Water (890 kg) was added and the slurry was aged for 2-3 h at 2-7° C. The solids were isolated by filtration, washed with a solution composed of 2-propanol (61 kg) and water (270 kg) and dried in vacuo at 50-60° C. to constant weight to afford 119.6 kg (90%) of the title compound.

Description 2b: Methyl (S)-5-(4-(benzyloxy)phenyl)-3,4-dihydro-2H-pyrrole-2-carboxylate (D2b) (Alternative Procedure)

A reactor was charged with methyl (S)-5-(4-(benzyloxy)phenyl)-2-((tert-butoxycarbonyl)amino)-5-oxopentanoate (532 kg) and ACN (1670 kg) and the slurry temperature was adjusted to 20-25° C. Methanesulfonic acid (346 kg (2.9 eq)) was added while maintaining a reaction temperature of <26° C. The contents of the reactor were stirred for 1 h; the progress of the reaction was monitored (HPLC). Upon completion, the contents of the reactor were cooled to <10° C. and a solution of 4.6N NH$_4$OH (773 kg) was added until a pH of 7-8 was reached while maintaining a reaction temperature of <25° C. The phases were separated and the upper organic layer was heated to 30-35° C. The organic layer was filtered through a plate filter to remove small particulates. While maintaining a reaction temperature of 30-35° C., 2-propanol (301 kg) and water (1277 kg) were added to the reactor. The solution was cooled to 18-22° C. and precipitation occurred. The slurry was stirred for at least 30 minutes at 18-22° C. and then cooled to 0-10° C. While maintaining a temperature of 0-10° C., water (2128 kg) was added and the reaction mixture was aged for not less than 2 hours at 0-10° C. The solids were isolated by filtration, washed with a solution composed of 2-propanol (188 kg) and water (798 kg) and dried in vacuo at 50-55° C. to constant weight to afford 319 kg (83%) of the title compound.

Description 2c: methyl (S)-5-(4-(benzyloxy)phenyl)-3,4-dihydro-2H-pyrrole-2-carboxylate—Flow Chemistry Procedure with MsOH/ACN

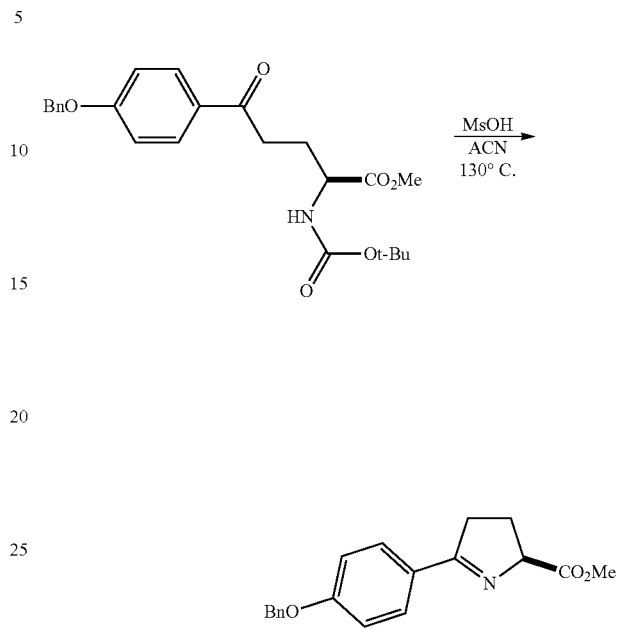

Solution A: 0.79M methanesulfonic acid in anhydrous ACN
Solution B: 0.25M 1-(tert-butyl) (S)-5-(4-(benzyloxy)phenyl)-2-((tert-butoxycarbonyl)amino)-5-oxopentanoate solution in anhydrous THF
Solution C: 4.6N NH$_4$OH solution in water
Equipment: plug flow reactor with a Y-mixer; 10 mL stainless steel reaction loop
Reaction Equivalents:
  solution A: 3.0 (3.764 mL/min)
  solution B: 1.0 (3.946 mL/min)
  solution C: 2.7 (0.579 mL/min)
Residence time: 1.3 min
Reaction temperature: 130° C.

After reaching steady state, the reaction stream was collected for 102 min in a 1 L flask immersed in an ice water bath. The base solution from pump C and the reaction stream were simultaneously collected with good stirring. Following the run, the pH was adjusted to 7 with by charging additional 4.6N ammonium hydroxide solution (about 15 mL). The phases were split, and the organic layer was concentrated to dryness by rotary evaporation in vacuo. The resulting residue was dissolved in ACN (120 mL) and distilled water (5 mL) at 25° C. and 500 rpm in a 100 mL EZMax reactor. The solution was cooled to 22° C. and water-IPA solution (2/1 (v/v), 80 mL) was added over about 30 min. The solution was further cooled to 18° C., seeded (5 wt %) and cooled to about 0° C. over 2 h. Water (139 mL) was added to the slurry over about 30 min, and the mixture was aged for about 20 min. The temperature of the slurry was raised to 20° C., held for about 40 min, re-cooled to about 0° C. over 90 min and aged for an additional 90 min. The solids were collected by filtration and dried to constant weight in vacuo at 55° C. to give 28.9 g (92%, corrected for seed) of the title compound.

Description 2d: methyl (S)-5-(4-(benzyloxy)phenyl)-3,4-dihydro-2H-pyrrole-2-carboxylate—Flow Chemistry Procedure with H$_2$SO$_4$/ACN

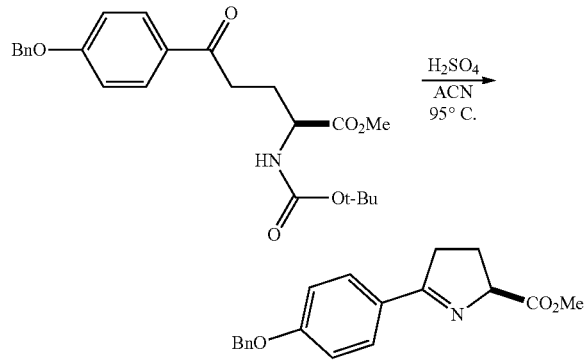

Three solutions were prepared for the flow reaction. Solution A: 0.25M 1-(tert-butyl) (S)-5-(4-(benzyloxy)phenyl)-2-((tert-butoxycarbonyl)amino)-5-oxopentanoate solution in anhydrous THF; Solution B: 0.75M sulfuric acid in anhydrous ACN;

A plug flow reactor with a Y-mixer and a 10 mL reaction loop was used with 1 reaction equivalent of solution A, and 2 reaction equivalents of solution B; a residence time of 7.5 minutes; a reaction temperature of 95° C.; and a collection time: 73.7 minutes (theory: 22.1 mmol title product).

The collected product stream was neutralized to pH 7-8 using 4.6N NH$_4$OH solution in water. HPLC analysis of the organic layer showed it contained 98.0 area % of the desired product. The lower organic layer was removed, and the organic layer was cooled to about 22° C., aged for about 30 min and cooled to 0-5° C. over about 1 h. Water (38 mL) was added over 10 min, and the resulting slurry was filtered, and was washed with a solution composed of IPA (0.45V) and water (1.5V). The solids were dried in vacuo at 55° C. to yield 2.62 g (38%) of the title compound.

Description 2e: methyl (S)-5-(4-(benzyloxy)phenyl)-3,4-dihydro-2H-pyrrole-2-carboxylate—Flow Chemistry Procedure with MsOH/THF-PhMe

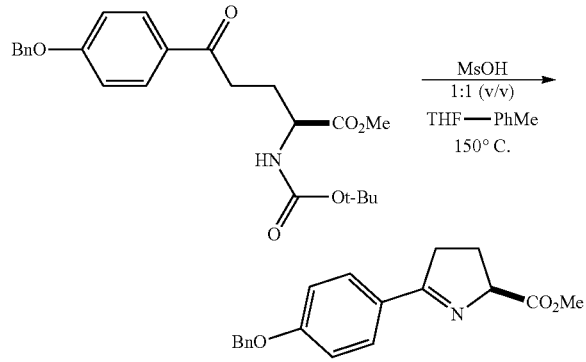

Solution A: 1.5M methanesulfonic acid in 1:1 (v/v) anhydrous THF-anhydrous PhMe
Solution B: 0.25M 1-(tert-butyl) (S)-5-(4-(benzyloxy)phenyl)-2-((tert-butoxycarbonyl)amino)-5-oxopentanoate solution in anhydrous THF Solution C: 4.6N NH$_4$OH solution in water
Equipment: plug flow reactor with a Y-mixer; 10 mL PFA coil reactor
Reaction Equivalents:
  solution A: 3.0 (1.667 mL/min)
  solution B: 1.0 (3.333 mL/min)
  solution C: 6.0 (1.087 mL/min)
Residence time: 2.0 min
Reaction temperature: 150° C.

After reaching steady state, the reaction stream was collected for 117 min in a 1 L flask immersed in an ice water bath. The base solution from pump C and the reaction stream were simultaneously collected with good stirring for the first 60 min; for the remainder of the collection time, only the reaction stream was collected. Following the run, the pH was adjusted to 7 with by charging additional 4.6N ammonium hydroxide solution. The phases were split, and the organic layer was concentrated to dryness by rotary evaporation in vacuo. The resulting residue was transferred to a 400 mL EZMax reactor using ACN (120 mL) and the temperature of the mixture was raised to 35° C. To the mixture was added water-IPA solution (2/1 (v/v), 78 mL) over about 10 min. The resulting solution was cooled to 18° C. over about 30 min, seeded (208 mg), further cooled to about 0° C. over 2 h and aged overnight. Water (135 mL) was added to the slurry over about 1 h, and the mixture was aged for about 4 h. The temperature of the slurry was raised to 13° C., re-cooled to about 0° C. over 3 h and aged overnight. The solids were collected by filtration and dried to constant weight in vacuo at 55° C. to give 8.18 g (27%, corrected for seed) of the title compound.

Description 2f: methyl (S)-5-(4-(benzyloxy)phenyl)-3,4-dihydro-2H-pyrrole-2-carboxylate—Method A

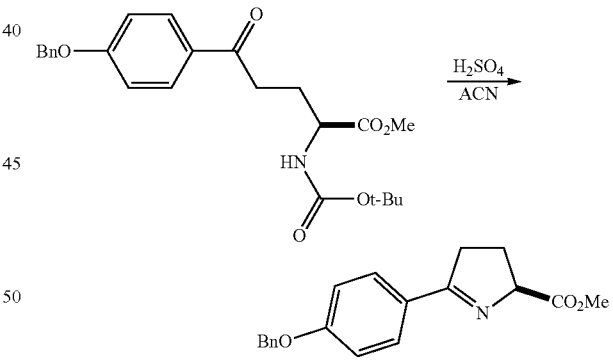

A reactor was charged with methyl (S)-5-(4-(benzyloxy)phenyl)-2-((tert-butoxycarbonyl)amino)-5-oxopentanoate (100.0 g) and ACN (400 mL) and the reaction temperature was adjusted to about 25° C. Concentrated sulfuric acid (45.3 g) was added over about 10 min while maintaining a reaction temperature of <50° C. The contents of the reactor were stirred at 40-50° C.; the progress of the reaction was monitored for completion (HPLC). Upon completion, the reaction was cooled to about 25° C. A solution of 4.6N NH$_4$OH (215 mL) was added with good stirring to a pH of about 7. The phases were separated, and the organic layer was split into two equal portions of about 256 mL for product isolation studies.

Portion A

To one portion was added a solution composed of 2-propanol (36.5 mL) and water (120 mL) with good stirring at about 22° C. The resulting slurry was aged briefly at 22° C., then cooled to 5° C. over about 1 h. Water (100 mL) was added to the slurry while maintaining a reaction temperature of <10° C. The solids were filtered, washed with a solution composed of 2-propanol (27.5 mL) and water (75 mL) and dried to constant weight in vacuo to give 30.87 g (85%) of the title compound.

Portion B

To one portion was added water (150 mL) with good stirring at about 22° C. The resulting slurry was aged briefly at 22° C., then cooled to 5° C. over about 1 h. Water (100 mL) was added to the slurry while maintaining a reaction temperature of <10° C. The solids were filtered, washed with a solution composed of 2-propanol (27.5 mL) and water (75 mL) and dried to constant weight in vacuo to give 31.90 g (88%) of the title compound.

Description 2g: methyl (S)-5-(4-(benzyloxy)phenyl)-3,4-dihydro-2H-pyrrole-2-carboxylate—Method B

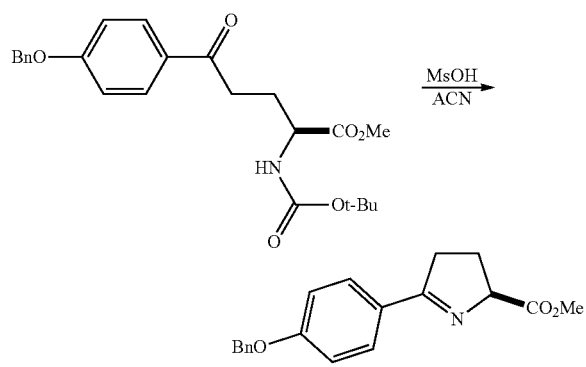

A reactor was charged with methyl (S)-5-(4-(benzyloxy)phenyl)-2-((tert-butoxycarbonyl)amino)-5-oxopentanoate (776.5 kg) and ACN (1743.5 kg) and the slurry temperature was adjusted to 15-25° C. Methanesulfonic acid (482.1 kg) was added while maintaining a reaction temperature of <26° C. The contents of the reactor were stirred at 20-25° C. for about 1 h. The progress of the reaction was monitored (HPLC); while awaiting results, the contents of the reactor were cooled to 0-10° C. A solution of 4.6N NH$_4$OH (590 kg) was added over about 25 min to a pH of 2-3 while maintaining a reaction temperature of <30° C. Additional 4.6N NH$_4$OH solution (519 kg) was added to a final pH of 7-8 while maintaining a reaction temperature of <25° C. The phases were separated and the upper organic layer was heated to 25-30° C. The organic layer was filtered and the filtrate was cooled to 20-25° C. While maintaining this temperature range, a solution of 2-propanol (362.8 kg) and water (924.3 kg) were added to the reactor. The solution was cooled to 15-20° C. and was seeded (3.7 kg, 0.5 wt %). The slurry was cooled to 0-5° C. over at least 2 h and aged for at least 30 min. Water (2403.1 kg) was added while maintain a reaction temperature of ≤20° C. The slurry was cooled to 0-5° C. and held for 30-40 min. The slurry was warmed to 15-20° C., aged for 30-40 min, cooled to 0-5° C. over at least 1 h and aged for at least 2 h. The solids were isolated by filtration, washed with a solution composed of 2-propanol (283.2 kg) and water (1079.5 kg) and dried in vacuo at 50-55° C. to constant weight to afford 466.0 kg (87%) of the title compound.

Description 3a: 1-(tert-butyl) 2-methyl (2S, 5R)-5-(4-hydroxyphenyl)pyrrolidine-1,2-dicarboxylate (D3)

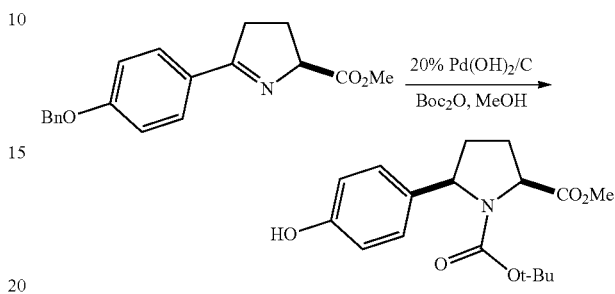

A hydrogenation reactor was charged with methyl (S)-5-(4-(benzyloxy)phenyl)-3,4-dihydro-2H-pyrrole-2-carboxylate (30 kg) and MeOH (120 kg), and the slurry was heated to solution at 30-40° C. The solution was cooled to 15-25° C. followed by addition of di-tert-butyldicarbonate (21.8 kg, 1.03 eq) and water wet 20% Pd(OH)$_2$/C (0.9 kg, 3 wt %). The contents of the reactor were degassed under vacuum followed by pressurization with nitrogen. The contents of the reactor were degassed under vacuum followed by pressurization with hydrogen (3-4 bar). After 2 h at 22-27° C., the reactor was vented and re-pressurized with hydrogen (3-4 bar). The progress of the reaction was monitored for completion (HPLC). After 4.5 h, the reactor was vented and MeOH (90 kg) was charged. The contents of the reactor were warmed to 32-42° C. and held for 20-30 min. The catalyst was removed by filtration through a bed of diatomite (13 kg) and the spent filter cake was washed with warm (40-45° C.) MeOH (25 kg). The combined filtrate and wash was concentrated in vacuo to 2 volumes at <40° C. and MeOH was charged (56 kg). The slurry was heated to 50-56° C. and the solution was aged for about 1.5 h. The solution was cooled to 20-30° C., the slurry was aged for about 1 h, water (60 kg) was added and the slurry was aged for about 2 h. The slurry was cooled to about −5° C. and aged for about 8 h. The solids were isolated by centrifugation, washed with 1:4 (v/v) MeOH-water (57.5 kg) and dried in vacuo at 50-60° C. to constant weight to afford 27.6 kg (88.5%) of the title compound.

Description 3b: 1-(tert-butyl) 2-methyl (2S, 5R)-5-(4-hydroxyphenyl)pyrrolidine-1,2-dicarboxylate—Method A

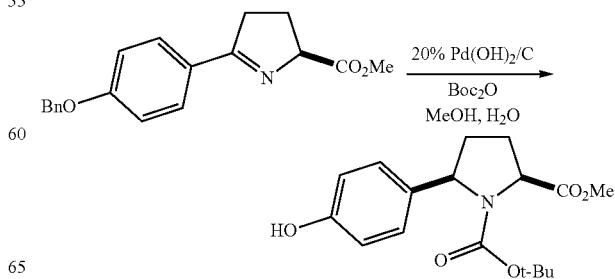

A hydrogenation reactor was charged with 20% Pd(OH)$_2$/C (water wet; 5.7 kg), methyl (S)-5-(4-(benzyloxy)phenyl)-3,4-dihydro-2H-pyrrole-2-carboxylate (186.4 kg), MeOH (8.85V), water (20 kg) and di-tert-butyldicarbonate (132 kg). The reactor was pressurized with nitrogen followed by venting (three times). The reactor was pressurized with hydrogen followed by venting (three times). The reactor was pressurized with hydrogen (15 bar). After about 2 h at 25° C., the reactor was vented and re-pressurized with hydrogen (15 bar). The progress of the reaction was monitored for completion (HPLC). After about 4.25 h, the reactor was vented and its contents were filtered, and the filtrate was concentrated in vacuo to about 4.4 volumes at about 35° C. and at about 240 mbar. The contents of the reactor were reheated to 55-60° C., the solution was cooled to 20-30° C. over about 2 h and the slurry was aged for about 1 h. Water (285 kg) was added over about 1 h and the slurry was aged for about 1 h. The slurry was cooled to 3-7° C. over about 2 h and aged for about 3 h. The solids were isolated by filtration, washed with 1:4 (v/v) MeOH-water (359 kg) and dried in vacuo at 50-55° C. to constant weight to afford 174.6 kg (90%) of the title compound.

Description 3c: 1-(tert-butyl) 2-methyl (2S, 5R)-5-(4-hydroxyphenyl)pyrrolidine-1,2-dicarboxylate—Method B

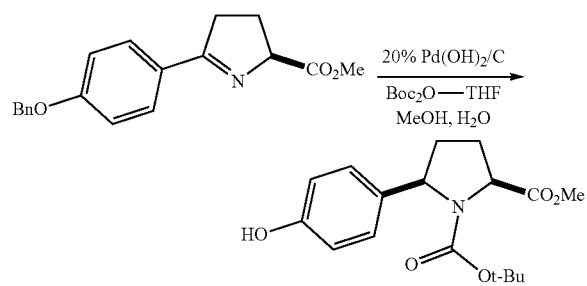

A hydrogenation reactor was charged with 20% Pd(OH)$_2$/C (water wet; 3 wt %), methyl (S)-5-(4-(benzyloxy)phenyl)-3,4-dihydro-2H-pyrrole-2-carboxylate (100 g), MeOH (4.5V), water (5 g) and 90 wt % di-tert-butyldicarbonate in THF (1.00 eq). The reactor was pressurized with nitrogen followed by venting (three times). The reactor was pressurized with hydrogen followed by venting (three times). The reactor was pressurized with hydrogen (15 bar). After 1 h at 25° C., the reactor was vented and re-pressurized with hydrogen (15 bar). The progress of the reaction was monitored for completion (HPLC). After 5 h, the reactor was vented and its contents were warmed to about 45° C. The catalyst was removed by filtration through a warmed filter, and the filtrate was re-heated to 45-55° C. and held for about 30 minutes. The filtrate was concentrated in vacuo to about 4.4 volumes at 30-40° C. The residue was cooled to 20-30° C. over at least 1 h, water (1.5V) was added over about 45 minutes and the slurry was aged for about 1 h. The slurry was cooled to 3-7° C. over about 2 h and aged for about 3 h. The solids were isolated by filtration, washed with 1:4 (v/v) MeOH-water (2V) and dried in vacuo at 50-60° C. to constant weight to afford 88.9 g (86%) of the title compound.

Description 3d: 1-(tert-butyl) 2-methyl (2S, 5R)-5-(4-hydroxyphenyl)pyrrolidine-1,2-dicarboxylate—Flow Chemistry Procedure

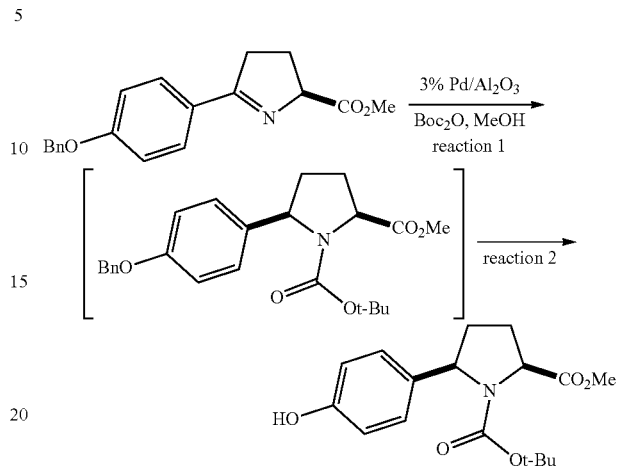

The flow direction was from top to bottom (feed solution and hydrogen); and the hydrogen flow rate was 50 mL/min (while maintaining desired reaction pressure).

A 25 mL tube was packed with glass wool, sand, spherical catalyst beads (3% Pd/e-Al$_2$O$_3$ (1.0-1.2 mm spherical pellets)), sand and glass wool to give a 10 mL packed bed volume. 4 wt % methyl (S)-5-(4-(benzyloxy)phenyl)-3,4-dihydro-2H-pyrrole-2-carboxylate and di-tert-butyldicarbonate (1.2 eq) in MeOH at −5° C. (feed solution 1) was then passed through the flow reactor at 0.08-0.10 mL/min, at a temperature of 53-61° C. and at a pressure of 10-15 bar. The collected solution contained a mixture of 1-(tert-butyl) 2-methyl (2S,5R)-5-(4-(benzyloxy)phenyl)pyrrolidine-1,2-dicarboxylate and 1-(tert-butyl) 2-methyl (2S, 5R)-5-(4-hydroxyphenyl)pyrrolidine-1,2-dicarboxylate in MeOH (feed solution 2) was passed through the flow reactor at 0.10 mL/min, at a temperature of 78-81° C. and at a pressure of 3 bar to produce about 600 g of a methanol solution primarily containing 1-(tert-butyl) 2-methyl (2S, 5R)-5-(4-hydroxyphenyl)pyrrolidine-1,2-dicarboxylate. This solution was concentrated in vacuo at a temperature of about 40° C. to a net weight of about 3.6× the amount of the input methyl (S)-5-(4-(benzyloxy)phenyl)-3,4-dihydro-2H-pyrrole-2-carboxylate. After stirring the mixture at ambient temperature for 15-20 min, water (2V) was added over about 30 min, the resulting mixture was aged for about 30 min, cooled to about 0° C. and aged for about 30 min. Solids were isolated by filtration, washed with ice cold 1:4 (v/v) MeOH-water (2×1V) and dried to constant weight in vacuo at 55° C. to afford 23.51 g (88%) of the title compound.

Description 4a: tert-butyl (2S, 5R)-2-carbamoyl-5-(4-((2-fluorobenzyl)oxy)phenyl)pyrrolidine-1-carboxylate (D4a) (K$_2$CO$_3$/ACN Procedure Using 2-fluorobenzyl Bromide)

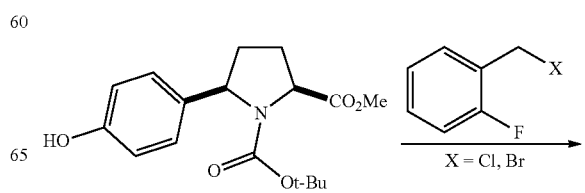

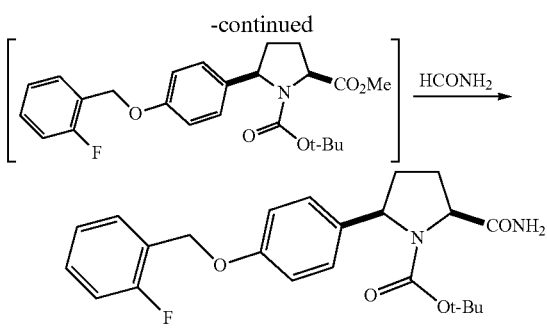

A reactor was charged with 1-(tert-butyl) 2-methyl (2S, 5R)-5-(4-hydroxyphenyl)pyrrolidine-1,2-dicarboxylate (110 kg), powdered K$_2$CO$_3$ (71.5 kg (1.5 equiv)) and ACN (429 kg). With good stirring, 2-fluorobenzyl bromide (68.2 kg (1.05 equiv)) and ACN (15 kg) were charged and the mixture was heated to 86-94° C.; the progress of the reaction was monitored (HPLC). Upon completion, the slurry was cooled to 40-50° C., filtered and the spent filter cake was washed with fresh ACN (175 kg).

To the ACN filtrate was charged powdered K$_2$CO$_3$ (94.6 kg (2.0 equiv)) and formamide (308 kg (20 equiv)) and the mixture was heated to 86-94° C.; the progress of the reaction was monitored (HPLC). Upon completion, the slurry was cooled to 70-75° C. and water (1150 kg) was added while maintaining a reaction temperature of >70° C. Following the addition the solution was aged for about 30 min, cooled to 65-70° C., seeded (0.55 kg) and aged for 3-4 h. The slurry was cooled to 50-60° C., aged 3-4 h, cooled to 20-30° C. and aged for 3-4 h. The solids were isolated by centrifugation, washed twice with water (220 kg) and dried in vacuo at 30-40° C. for 4-8 h and at 50-60° C. for 4-8 h to yield 128.75 kg (87.5%) of the title compound.

Description 4b: tert-butyl (2S, 5R)-2-carbamoyl-5-(4-((2-fluorobenzyl)oxy)phenyl)pyrrolidine-1-carboxylate (D4b) (NaOMe-MeOH Procedure Using 2-fluorobenzyl Bromide in DMF)

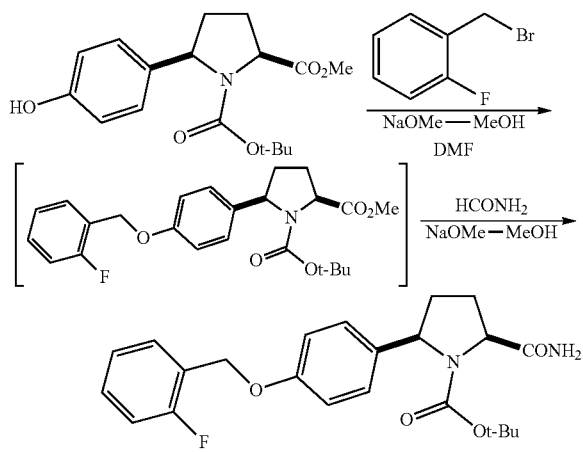

A reactor was charged with 1-(tert-butyl) 2-methyl (2S, 5R)-5-(4-hydroxyphenyl)pyrrolidine-1,2-dicarboxylate (1.0 kg), anhydrous DMF (2.9 L), 2-fluorobenzyl bromide (430 mL (1.12 equiv)) and anhydrous DMF (0.1 L). The solution was cooled to about 15° C. With good stirring, 741 mL (1.05 equiv) 4.4M NaOMe-MeOH solution was added while maintaining a temperature of ≤20° C. Following the charge, the contents of the reactor were warmed to about 25° C., aged for about 1 h and 44 mL (0.06 equiv) 4.4M NaOMe-MeOH solution was added over about 5 min. The progress of the reaction was monitored (HPLC).

Upon completion, formamide (2.5 L) was charged followed by addition of 811 mL (1.15 equiv) 4.4M NaOMe-MeOH solution while maintaining a temperature of ≤25° C. The contents of the reactor were aged for about 1 h and 516 mL (0.73 equiv) 4.4M NaOMe-MeOH solution was added while maintaining a temperature of ≤25° C. The progress of the reaction was monitored (HPLC). Upon completion, a solution of glacial acetic acid (350 mL (2.0 equiv) in water (2.2 L)) was added over about 10 min. The slurry was heated to about 70° C. and aged for about 1 h. Water (1.8 L) was added over about 1 h and the slurry was cooled to about 3° C. over 3 h and aged for about 10 h. The solids were isolated by filtration, washed twice with water (2 L) and dried to constant weight in vacuo at 80° C. to afford 1.21 kg (94%) of the title compound.

Description 4c: tert-butyl (2S, 5R)-2-carbamoyl-5-(4-((2-fluorobenzyl)oxy)phenyl)pyrrolidine-1-carboxylate (D4c) (NaOMe-MeOH Procedure Using 2-fluorobenzyl Bromide in DMF) (Alternative Procedure)

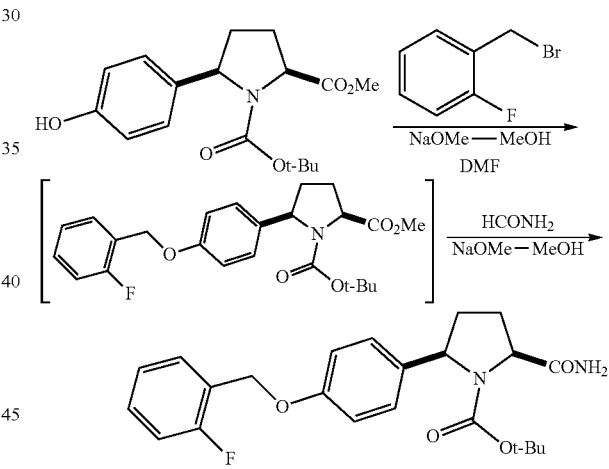

A reactor was charged with 1-(tert-butyl) 2-methyl (2S, 5R)-5-(4-hydroxyphenyl)pyrrolidine-1,2-dicarboxylate (100 g), anhydrous DMF (290 mL), 2-fluorobenzyl bromide (42.2 mL (1.10 equiv)) and anhydrous DMF (10 mL). The solution was cooled to about 15° C. With good stirring, 75 mL (1.06 equiv) 4.4M NaOMe-MeOH solution was added over a period of approximately 30 min while maintaining a temperature of ≤20° C. Following the charge, the contents of the reactor were warmed to about 25° C. and aged for about 2 h. The progress of the reaction was monitored (HPLC).

Upon completion, formamide (250 mL) was charged followed by addition of 133 mL (1.88 equiv) 4.4M NaOMe-MeOH solution over approximately 45 min while maintaining a temperature of ≤25° C. The contents of the reactor were aged for about 4 h. The progress of the reaction was monitored (HPLC). Upon completion, a solution of glacial acetic acid (35 mL (2.0 equiv) in water (100 mL) was added over about 30 min. The slurry was heated to about 60° C. Water (300 mL) was then charged to the reactor over about 1 h, and the slurry was aged for about 1 h. The slurry was cooled to about 3° C. over 3 h and aged for about 1 h. The solids were isolated by filtration, washed twice with water (200 mL) and dried to constant weight in vacuo at 80° C. to afford 120.0 g (93%) of the title compound.

Description 4d: tert-butyl (2S, 5R)-2-carbamoyl-5-(4-((2-fluorobenzyl)oxy)phenyl)pyrrolidine-1-carboxylate (D4d) (NaOMe-MeOH Procedure Using 2-fluorobenzyl Chloride in DMF)

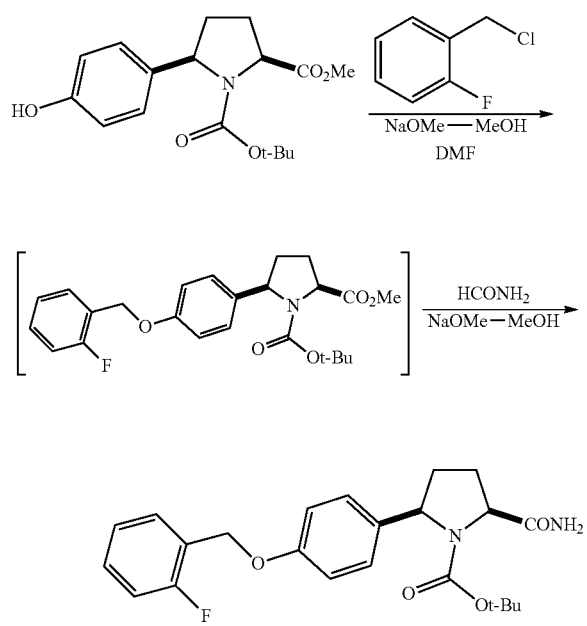

A reactor was charged with 1-(tert-butyl) 2-methyl (2S, 5R)-5-(4-hydroxyphenyl)pyrrolidine-1,2-dicarboxylate (7.50 g), anhydrous DMF (22.5 mL) and 2-fluorobenzyl chloride (3.20 mL (1.15 equiv)). The solution was cooled to about 15° C. With good stirring, 5.6 mL (1.06 equiv) 4.4M NaOMe-MeOH solution was added while maintaining a temperature of <25° C.

Following the charge, the contents of the reactor were warmed to about 45° C. over 20 min. The progress of the reaction was monitored (HPLC).

Upon completion, the contents of the reactor were cooled to about 25° C. over about 10 min. Formamide (19 mL) was charged followed by addition of 5.8 mL (1.1 equiv) 4.4M NaOMe-MeOH solution while maintaining a temperature of <25° C. The contents of the reactor were aged for about 1 h and 3.7 mL (0.7 equiv) 4.4M NaOMe-MeOH solution was added while maintaining a temperature of <25° C. The progress of the reaction was monitored (HPLC). Upon completion, a solution of glacial acetic acid (2.6 mL (2.0 equiv)) in water (7.5 mL) was added over about 25 min. The slurry was heated to about 65° C. and water (22.5 mL) was added to the solution over about 1 h. The slurry was aged for about 30 min, was cooled to 0-5° C. over about 3 h and aged for about 30 min. The solids were isolated by filtration, washed twice with water (7.5 mL) and dried to constant weight in vacuo at 80° C. to afford 8.39 g (90%) of the title compound.

Description 4e: tert-butyl (2S, 5R)-2-carbamoyl-5-(4-((2-fluorobenzyl)oxy)phenyl)pyrrolidine-1-carboxylate (D4e) (NaOMe-MeOH Procedure Using 2-fluorobenzyl Chloride in DMSO)

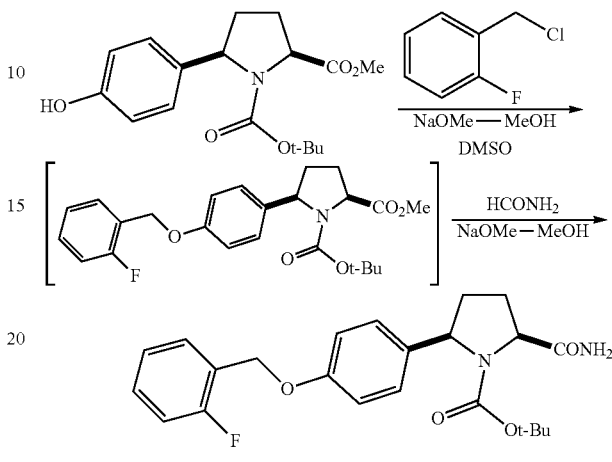

A reactor was charged with 1-(tert-butyl) 2-methyl (2S, 5R)-5-(4-hydroxyphenyl)pyrrolidine-1,2-dicarboxylate (7.50 g), anhydrous DMSO (22.5 mL) and 2-fluorobenzyl chloride (3.20 mL (1.15 equiv)). The solution was cooled to about 15° C. With good stirring, 5.5 mL (1.06 equiv) 4.5M NaOMe-MeOH solution was added while maintaining a temperature of <25° C. Following the charge, the contents of the reactor were warmed to about 25° C. over 5 min. The progress of the reaction was monitored (HPLC).

Upon completion, formamide (19 mL) was charged followed by addition of 9.73 mL (1.88 equiv) 4.5M NaOMe-MeOH solution over about 45 min. The progress of the reaction was monitored (HPLC). Upon completion, a solution of glacial acetic acid (2.6 mL (2.0 equiv)) in water (7.5 mL) was added over about 25 min. The slurry was heated to about 65° C. and water (22.5 mL) was added to the solution over about 1 h. The slurry was aged for about 30 min, was cooled to 0-5° C. over about 3 h and aged for about 30 min. The solids were isolated by filtration, washed twice with water (7.5 mL) and dried to constant weight in vacuo at 80° C. to afford 8.72 g (90%) of the title compound.

Description 4f: tert-butyl (2S, 5R)-2-carbamoyl-5-(4-((2-fluorobenzyl)oxy)phenyl)pyrrolidine-1-carboxylate (D4f) (t-BuOK Procedure Using 2-Fluorobenzyl Bromide in ACN-formamide)

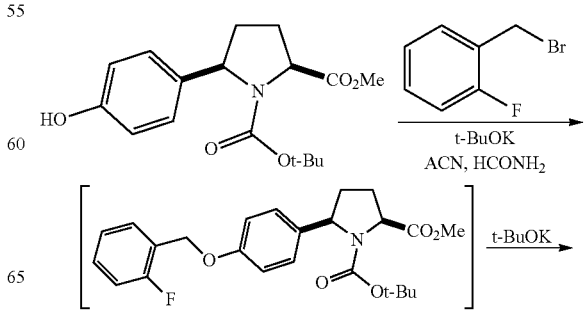

-continued

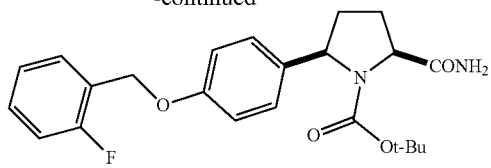

A reactor was charged with 1-(tert-butyl) 2-methyl (2S, 5R)-5-(4-hydroxyphenyl)pyrrolidine-1,2-dicarboxylate (10.0 g), anhydrous ACN (30 mL), 2-fluorobenzyl bromide (4.18 mL (1.05 equiv)) and formamide (10 mL). The solution was cooled to 0-5° C. With good stirring, 3.67 g (1.05 equiv) t-BuOK was added followed by warming the contents of the reactor to about 15° C. The progress of the reaction was monitored (HPLC).

Upon completion, the contents of the reactor were cooled to 0-5° C. and 4.71 g (1.35 equiv) t-BuOK was added followed by warming the contents of the reactor to about 15° C. The progress of the reaction was monitored (HPLC). Upon completion, the contents of the reactor were warmed to about 65° C. and a solution of glacial acetic acid (4.14 mL (2.3 equiv)) in water (10 mL) was added. Additional water (40 mL) was added over about 30 min. The contents of the reactor were cooled to 0-5° C. and filtered. The filter cake was washed twice with water (10 mL) and dried to constant weight in vacuo at 80° C. to afford 10.93 g (85%) of the title compound.

Description 4g: tert-butyl (2S, 5R)-2-carbamoyl-5-(4-((2-fluorobenzyl)oxy)phenyl)pyrrolidine-1-carboxylate (D4g) (t-BuONa Procedure Using 2-Fluorobenzyl Bromide in ACN-formamide)

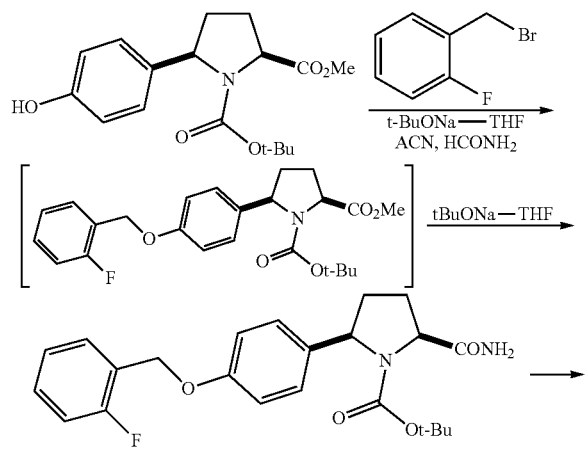

A reactor was charged with 1-(tert-butyl) 2-methyl (2S, 5R)-5-(4-hydroxyphenyl)pyrrolidine-1,2-dicarboxylate (10.0 g), anhydrous ACN (30 mL), 2-fluorobenzyl bromide (4.18 mL (1.05 equiv)) and formamide (1.5 mL). The solution was cooled to 0-5° C. With good stirring, 16.4 mL (1.05 equiv) 2M t-BuONa-THF solution was added followed by warming the contents of the reactor to about 15° C. The progress of the reaction was monitored (HPLC).

Upon completion, the contents of the reactor were cooled to 0-5° C. and formamide (8.5 mL) was added, followed by 21 mL (1.35 equiv) 2M t-BuONa-THF solution, and the contents of the reactor were warmed to about 15° C. The progress of the reaction was monitored (HPLC). Upon completion, the contents of the reactor were warmed to about 65° C. and a solution of glacial acetic acid (4.14 mL (2.3 equiv)) in water (10 mL) was added. Additional water (40 mL) was added over about 30 min. The contents of the reactor were cooled to 0-5° C. and filtered. The filter cake was washed twice with water (10 mL) and dried to constant weight in vacuo at 80° C. to afford 11.06 g (86%) of the title compound.

Description 4h: tert-butyl (2S, 5S)-2-carbamoyl-5-(4-((2-fluorobenzyl)oxy)phenyl)pyrrolidine-1-carboxylate—Method A

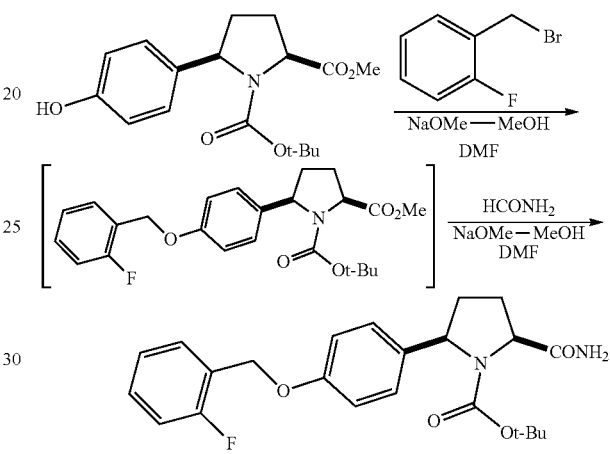

A reactor was charged with 1-(tert-butyl) 2-methyl (2S, 5R)-5-(4-hydroxyphenyl)pyrrolidine-1,2-dicarboxylate (264 Kg), anhydrous DMF (748 kg) and 2-fluorobenzyl bromide (171 Kg (1.10 eq)). The solution was cooled to about 15° C. With good stirring, 157 Kg (1.06 eq) 30% NaOMe-MeOH solution was added over at least 30 min while maintaining a temperature between 20-30° C. Following the charge, the line was rinsed forward with MeOH (18 kg), and the batch was maintained at about 25° C. for at least 1 h. The progress of the reaction was monitored for completion (HPLC).

Upon completion, formamide (749 Kg) was charged followed by a line rinse with MeOH (18 kg). 279 Kg (1.88 eq) 30% NaOMe-MeOH solution was added over at least 45 min while maintaining a temperature of about 25° C. followed by a line rinse with MeOH (18 kg). The contents of the reactor were maintained at about 25° C. with agitation for about 4 h. The progress of the reaction was monitored for completion (HPLC). Upon completion, the batch was transferred to a second reactor and the equipment was rinsed forward with MeOH (155 Kg). Glacial acetic acid (97 Kg) was added to the batch over at least 15 min while maintaining a temperature of 20-30° C. followed by the addition of water (264 Kg). The batch was heated to 60° C. and water (792 Kg) was added over at least 2 h with good agitation. The batch was maintained at 60° C. with agitation for at least 1 h. The batch was cooled to about 2° C. over at least 3 h and aged for at least 1 h. The solids were isolated by filtration and washed twice with water (528 Kg per wash). The wet cake was dried to constant weight in vacuo at 67° C. to afford 315.4 kg (93%) of the title compound.

Description 4i: tert-butyl (2S, 5S)-2-carbamoyl-5-(4-((2-fluorobenzyl)oxy)phenyl)pyrrolidine-1-carboxylate—Method B

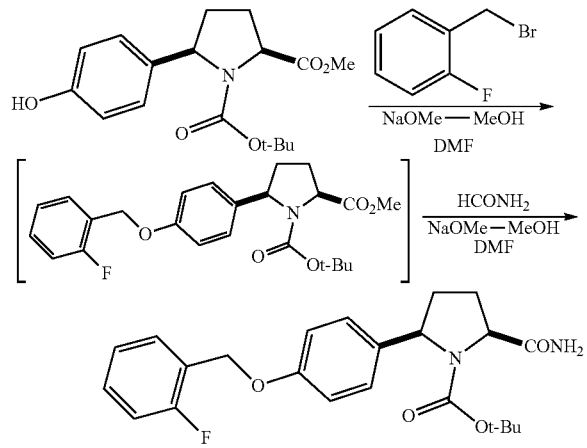

A reactor was charged with 1-(tert-butyl) 2-methyl (2S, 5R)-5-(4-hydroxyphenyl)pyrrolidine-1,2-dicarboxylate (70 g), anhydrous DMF (198.2 g) and 2-fluorobenzyl bromide (45.3 g (1.10 equiv)). With good agitation, 41.4 g (1.06 equiv) 30% NaOMe-MeOH solution was added over about 60 min while maintaining a temperature of 20-30° C. The addition funnel was rinsed forward into the reactor with MeOH (2.4 g). The batch was maintained at about 25° C. for at least 1 h; the progress of the reaction was monitored for completion (HPLC).

Upon completion, formamide (238.1 g) was charged followed by rinsing forward the charging equipment with MeOH (2.4 g). 30% NaOMe-MeOH solution (66.5 g (1.70 equiv)) was added over 45 min while maintaining temperature at about 25° C. The addition funnel was rinsed forward into the reactor with MeOH (2.4 g). The batch was stirred for about 4 h at 25° C.; the progress of the reaction was monitored for completion (HPLC). Upon completion, the batch was transferred to a second reactor and the equipment was rinsed forward with MeOH (20.6 g). Glacial acetic acid (25.7 g) was added while maintaining a temperature of 20-30° C. Water (70 g) was added over about 20 min and the batch was heated to 60° C. Water (280 g) was added over at least 2 h with good agitation. The batch was maintained at 60° C. with agitation for at least 1 h, cooled to 0-3° C. over at least 3 h and aged for at least 1 h. The solids were isolated by filtration, washed with water/MeOH 70:30 v/v (140 mL) and water (140 g). The wet cake was dried to constant weight in vacuo at 80° C. to afford 83.7 g (93%) of the title compound.

Description 5a: (2S,5R)-5-(4-((2-fluorobenzyl)oxy)phenyl)pyrrolidine-2-carboxamide (E1)

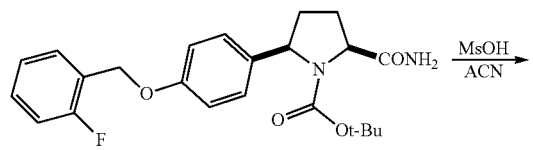

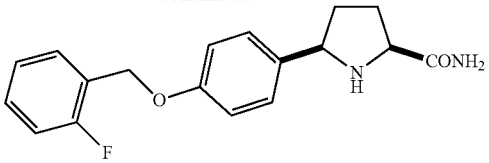

A reactor was charged with tert-butyl (2S, 5R)-2-carbamoyl-5-(4-((2-fluorobenzyl)oxy)phenyl)pyrrolidine-1-carboxylate (which may be prepared as described in Description 4) (375.1 kg) and ACN (825.6 kg). With good agitation, methanesulfonic acid (114.8 kg (1.3 equiv) was added while maintaining a reaction temperature of 20-25° C. followed by ACN (50 kg). The contents of the reactor were warmed to 40-50° C. and aged for 2-3 h. The progress of the reaction was monitored (HPLC). Upon completion, a solution of 1.0N NH$_4$OH (377 kg) was added while maintaining a reaction temperature of 40-50° C. The reaction temperature was raised to 48-52° C. and 1.0N NH$_4$OH (1495 kg) was added slowly with good stirring while maintaining the reaction temperature within this range. The slurry was cooled to −3 to 3° C. over 3-4 h and was aged for 1-2 h. The solids were isolated by centrifugation (3 drops) and each portion was washed twice with water (182-189 kg). The solids were dried in vacuo at 30° C. for 4 h, at 50° C. for 4 h and to constant weight at 80° C. (10 h) to afford 256.4 kg (90.5%) of the title compound.

Description 5b: (2S,5R)-5-(4-((2-fluorobenzyl)oxy)phenyl)pyrrolidine-2-carboxamide hydrochloride (1:1) (E2)

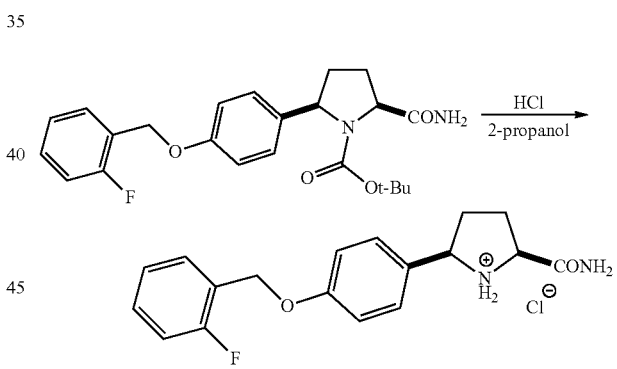

A reactor was charged with 2-propanol (672 kg) and the solvent was cooled to −10 to 0° C. With good agitation, HCl (90 kg) was introduced while maintaining a reaction temperature of −10-0° C. A sample of the solution was removed for concentration determination.

A reactor was charged with tert-butyl (2S, 5R)-2-carbamoyl-5-(4-((2-fluorobenzyl)oxy)phenyl)pyrrolidine-1-carboxylate (which may be prepared as described in Description 4) (160 kg) and 2-propanol (1280 kg). With good agitation, the prepared HCl-2-propanol solution (5.3 eq) was added while maintaining a reaction temperature of 20-30° C. The contents of the reactor were warmed to 30-35° C. and aged for 12-16 h. The progress of the reaction was monitored (HPLC). Upon completion, the contents of the reactor were cooled to 0-10° C., concentrated and aged for 2-3 h at 0-10° C. The solids were filtered, washed with 2-propanol (105 kg) and dried in vacuo at 60-70° C. for 15-20 h to afford 132 kg (96%) of the title compound.

Description 5c: (2S,5R)-5-(4-((2-fluorobenzyl)oxy)phenyl)pyrrolidine-2-carboxamide—Method A

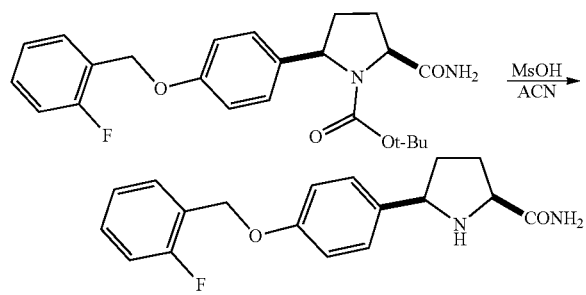

A reactor was charged with tert-butyl (2S, 5S)-2-carbamoyl-5-(4-((2-fluorobenzyl)oxy)phenyl)pyrrolidine-1-carboxylate (307 Kg) and acetonitrile (612 Kg). With good agitation, methanesulfonic acid (30 Kg (1.28 equiv)) was added over at least 30 min while maintaining a reaction temperature of 20-30° C. The batch was warmed to 30° C., aged for about 30 min and heated to 45° C. over about 30 min. The batch was maintained at 45° C. for 2 h; the progress of the reaction was monitored for completion (HPLC). Upon completion, the batch was transferred to a second reactor, rinsed forward with acetonitrile (108 Kg) and 1.7% aqueous NH$_4$OH solution (304 Kg) was added while maintaining a temperature of about 40-50° C. The reaction temperature was raised to about 46-52° C. and 1.7% NH$_4$OH solution (1216 Kg) was added slowly over 2 h with good stirring while maintaining the reaction temperature within this range. The batch was aged at 50° C. for about 1 h, cooled to 0° C. over at least 3 h and aged for about 1 h. The solids were isolated by filtration and washed twice with water (614 Kg per wash). The solids were dried in vacuo at 70° C. to constant weight to afford 218 Kg (94%) of the title compound.

Description 5d: (2S,5R)-5-(4-((2-fluorobenzyl)oxy)phenyl)pyrrolidine-2-carboxamide—Method B

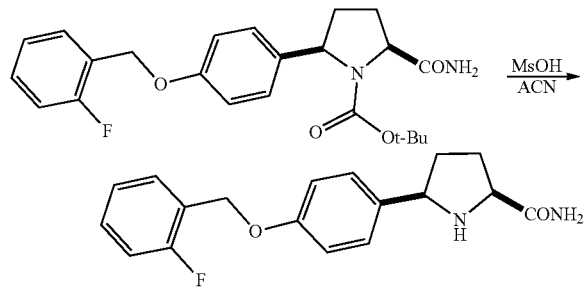

A reactor was charged with tert-butyl (2S, 5S)-2-carbamoyl-5-(4-((2-fluorobenzyl)oxy)phenyl)pyrrolidine-1-carboxylate (100 g) and ACN (199.5 g). With good agitation, methanesulfonic acid (29.7 g (1.28 equiv)) was added while maintaining a reaction temperature of 20-30° C. The batch was warmed to 30° C., aged for at least 30 min and heated to 45° C. over at least 30 min. The batch was maintained at 45° C. for 2 h; the progress of the reaction was monitored for completion (HPLC). Upon completion, the batch was transferred to a second reactor; the first reactor was rinsed forward with ACN (35.4 g). A solution of 1.7% aqueous NH$_4$OH (99.0 g) was added at 40-50° C. over at least 15 min. The reaction temperature was raised to 49° C. and 1.7% NH$_4$OH solution (396.0 g) was added slowly over at least 2 h with good stirring while maintaining the reaction temperature at about 49° C. The slurry was aged for 30-90 min, cooled to 0° C. over 3 h and aged for at least 1 h. The solids were isolated by filtration and washed with water/acetonitrile 90:10 v/v (200 mL) and water (200 g). The solids were dried in vacuo at 70° C. to constant weight to afford 71.6 g (94%) of the title compound.

Description 5e: (2S,5R)-5-(4-((2-fluorobenzyl)oxy)phenyl)pyrrolidine-2-carboxamide Hydrochloride

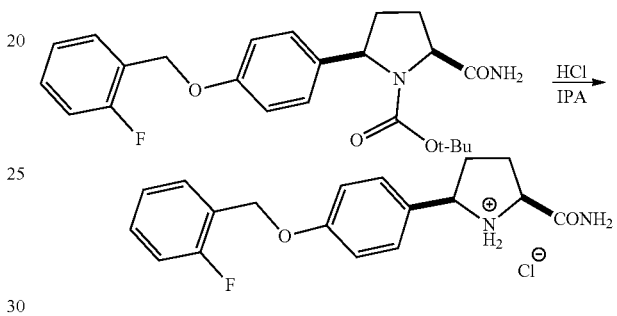

A reactor was charged with tert-butyl (2S, 5S)-2-carbamoyl-5-(4-((2-fluorobenzyl)oxy)phenyl)pyrrolidine-1-carboxylate (160 kg) and isopropanol (1280 kg) at 20-30° C. A solution of 2.6M HCl in isopropanol (5.3 eq) was added over about 2 h at 20-35° C. The contents of the reactor were warmed to 30-35° C., and the progress of the reaction was monitored for completion (HPLC). The contents of the reactor were cooled to about 10° C. over about 3 h, concentrated in vacuo for about 1 h and aged at 5-10° C. for about 2 h under an inert atmosphere of nitrogen. Solids were filtered, washed with isopropanol (125 kg) and dried to constant weight in vacuo at 60-70° C. to give 132.05 kg (96%) of the title compound.

Description 6a: 1-(tert-butyl) 2-methyl (2S, 5R)-5-(4-hydroxyphenyl)pyrrolidine-1,2-dicarboxylate—Method A

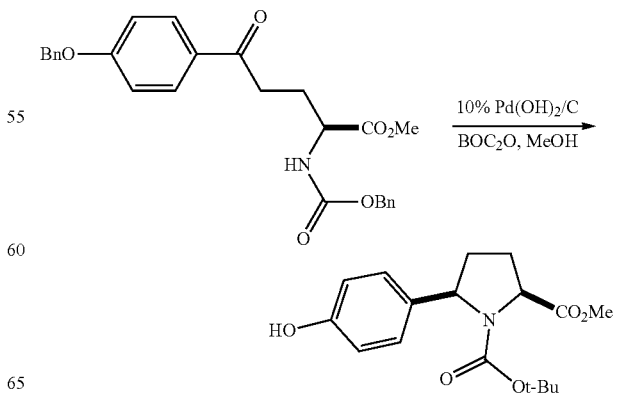

A hydrogenation reactor was charged with 10% Pd(OH)$_2$/C (water wet; 1.06 g), benzyl (S)-5-(4-(benzyloxy)phenyl)-2-((tert-butoxycarbonyl)amino)-5-oxopentanoate (23 g), MeOH (140 mL) and di-tert-butyldicarbonate (11.3 g, 1.02 eq). The reactor was pressurized with hydrogen (8 bar) and stirred (300 rpm) for 3 h at ambient temperature followed by stirring at 50° C. for an additional 5 h. The contents of the reactor were cooled to ambient temperature and filtered. The filtrate was concentrated to dryness and the residue was reconstituted in warm MeOH (30 mL). The contents of the flask were cooled to ambient temperature. The solids were isolated by filtration and dried in vacuo at 60° C. to constant weight to afford 9.6 g (60%) of the title compound.

Description 6b: 1-(tert-butyl) 2-methyl (2S, 5R)-5-(4-hydroxyphenyl)pyrrolidine-1,2-dicarboxylate—Method B

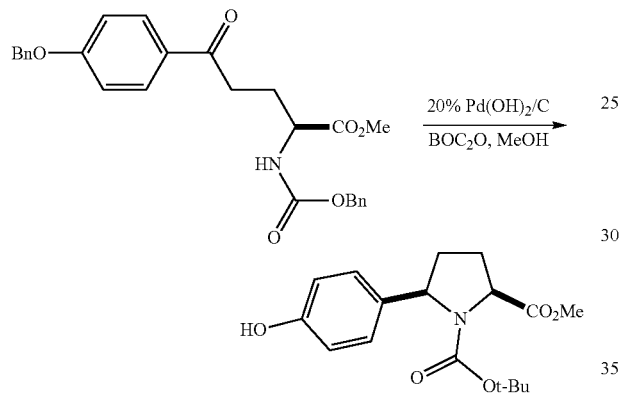

A hydrogenation reactor was charged with 20% Pd(OH)$_2$/C (water wet; 2.25 g), benzyl (S)-5-(4-(benzyloxy)phenyl)-2-((tert-butoxycarbonyl)amino)-5-oxopentanoate (74.59 g (71.00 g activity)), di-tert-butyldicarbonate (35.27 g, 1.01 eq) and MeOH (415 g). Following three vacuum/nitrogen break cycles, the reactor was pressurized with hydrogen (4 bar) and stirred (~2200 rpm) for about 105 min at 25° C., then heated to 35° C. and held for an additional 1 h. The reactor was vented, additional MeOH (59 g) was charged, and the reduction was continued at 35° C., 4 bar and ~2200 rpm. The progress of the reaction was monitored for completion (HPLC). Celite® (2.5 g) was added, and the mixture was filtered through a pad of Celite® (2.5 g) and the spent pad was washed with warm MeOH (59 g). The filtrate was concentrated at 40° C. and 200 mbar to a net weight of about 179 g. The contents of the flask were warmed to solution at about 55° C., slowly cooled to ambient temperature and aged for about 30 min. Water (100 g) was added over about 1 h, and the mixture was aged overnight at ambient temperature. The mixture was cooled to 0-5° C., aged for about 3 h and filtered. The solids were washed with cold 1:4 (v/v) MeOH-water (2×48 g) and dried in vacuo at 55° C. to constant weight to afford 43.98 g (89%) of the title compound.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A process for preparing a compound of formula (I)

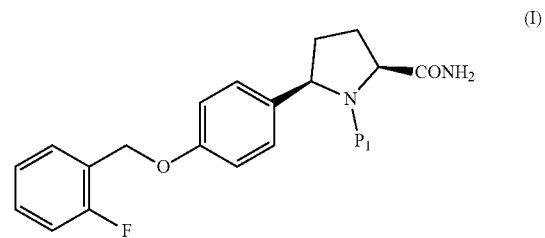

by reacting a compound of formula (II) with formamide:

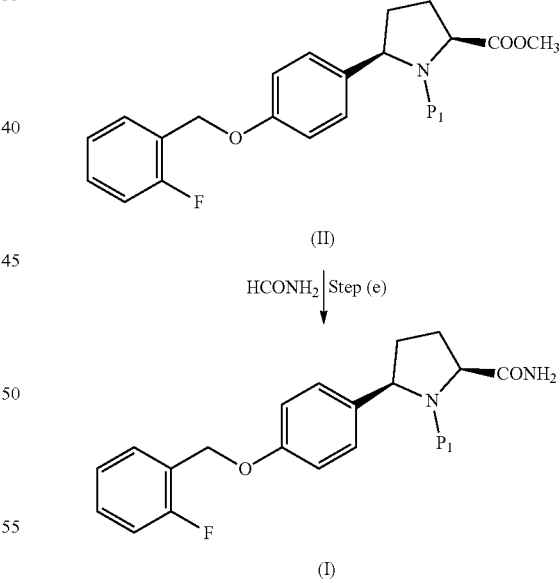

wherein P$^1$ is a protecting group selected from: tert-butyloxycarbonyl (BOC); 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps, and trifluoroacetyl.

2. The process of claim 1, further comprising preparing a compound of formula (III)$^a$ by deprotecting the compound of formula (I):

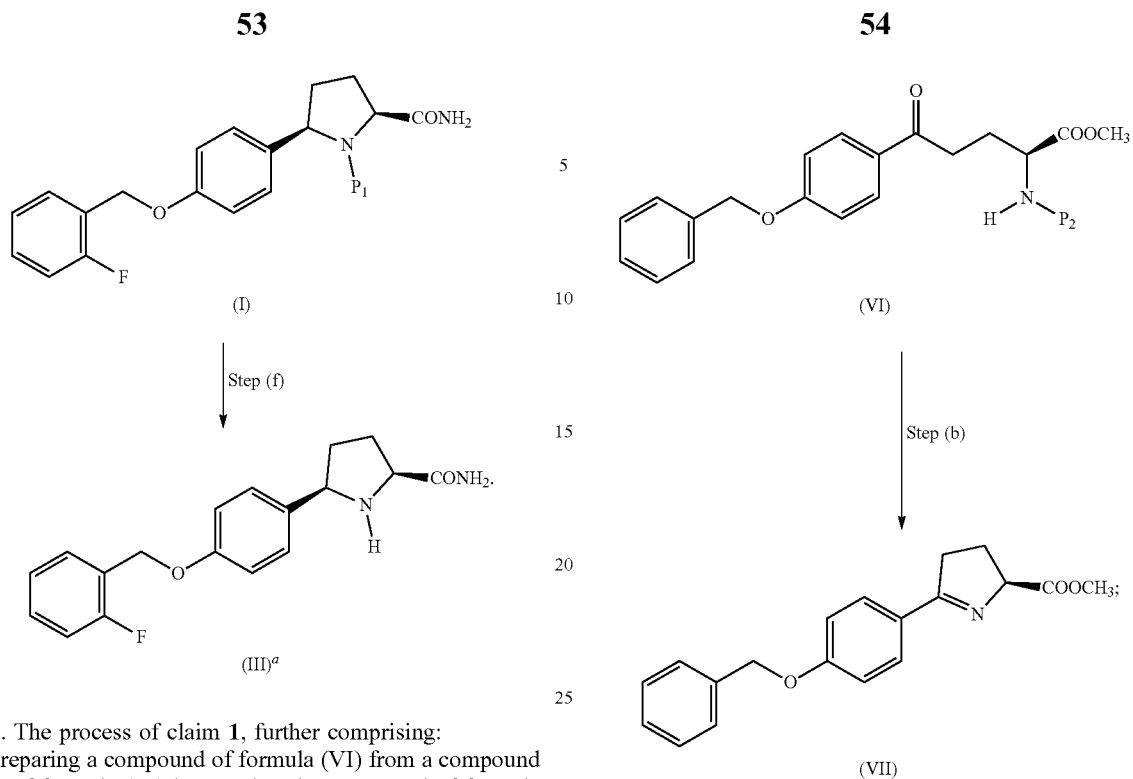

3. The process of claim 1, further comprising:
preparing a compound of formula (VI) from a compound of formula (IV) by reacting the compound of formula (IV) with a compound of formula (V):

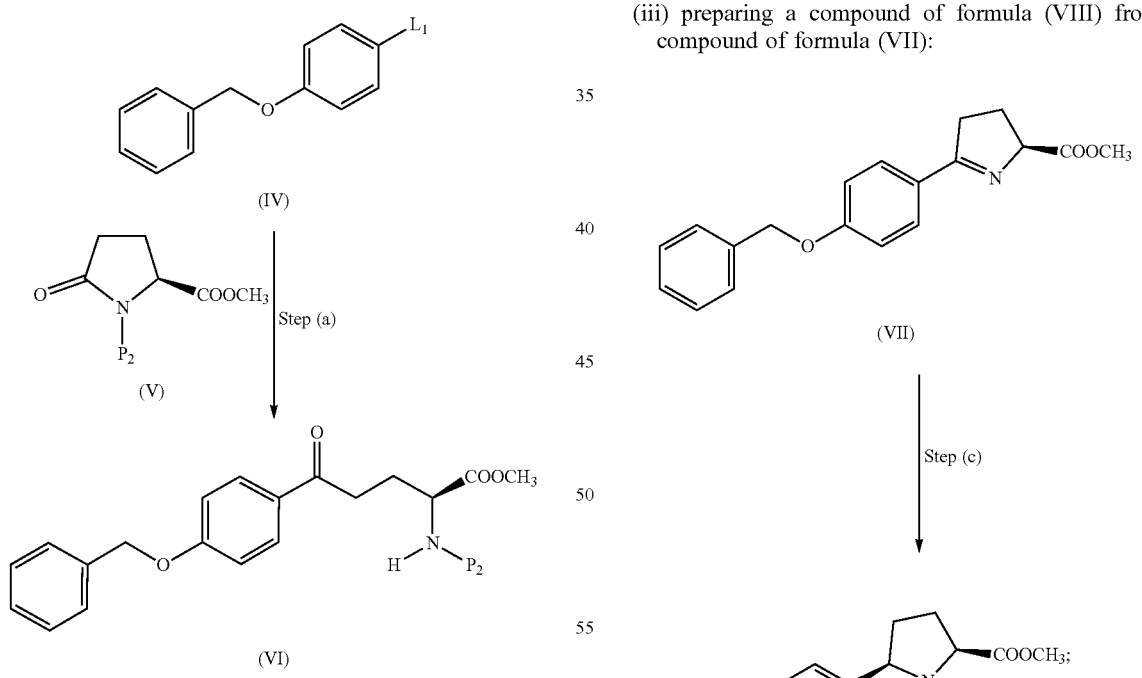

wherein $P_2$ is a protecting group selected from: tert-butyloxycarbonyl (BOC); 9-fluorenylmethyloxycarbonyl (FMOC); acetyl (Ac); benzoyl (Bz); benzyloxycarbonyl; carbamates; p-methoxyphenyl (PMP); tosyl (Ts); a sulfonamide selected from Nosyl and Nps, and trifluoroacetyl and $L^1$ represents a leaving group; followed by (ii) preparing a compound of formula (VII) from a compound of formula (VI):

followed by (iii) preparing a compound of formula (VIII) from a compound of formula (VII):

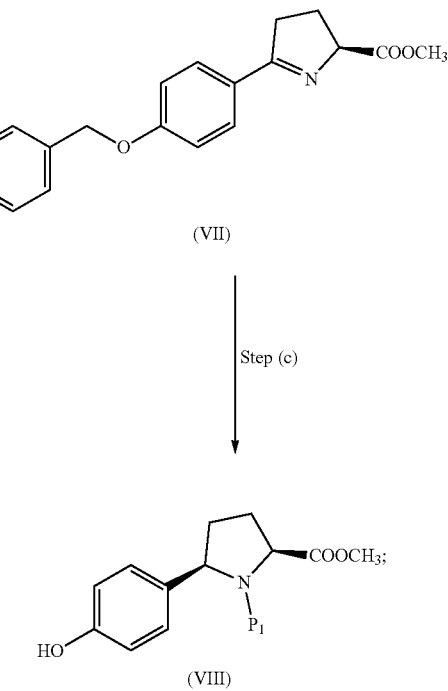

followed by (iv) preparing a compound of formula (II) by reacting a compound of formula (VIII) with a compound of formula (IX):

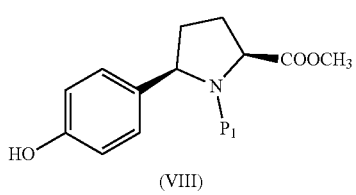

(VIII)

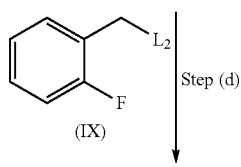

(IX)

Step (d)

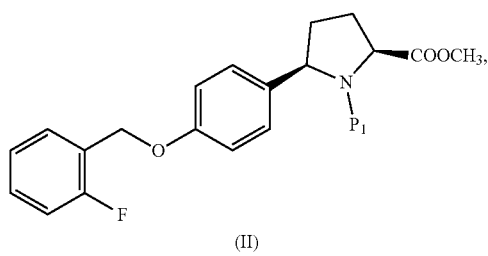

(II)

wherein L₂ represents a leaving group.

4. The process of claim 3, wherein $P_2$ is a protecting group selected from: tert-butyloxycarbonyl (BOC); 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps, and trifluoroacetyl.

5. The process of claim 4, wherein $P_2$ is tert-butyloxycarbonyl (BOC).

6. The process of claim 3, wherein $L_1$ is a halogen atom.

7. The process of claim 3, wherein step (a) comprises the use of 1) isopropyl magnesium chloride (i-PrMgCl) and a solvent in addition to an n-butyllithium (n-BuLi) hexane solution; or 2) an isopropyl magnesium chloride (i-PrMgCl) lithium chloride complex and a solvent in addition to bis(dimethylamino)ethyl ether.

8. The process of claim 7, wherein step (a) is conducted via a continuous or flow process.

9. The process of claim 7, wherein $L_1$ represents magnesium bromide.

10. The process of claim 3, wherein step (b) comprises the use of methanesulfonic acid or sulfuric acid in acetonitrile; or methanesulfonic acid in 1:1 (v/v) tetrahydrofuran-PhMe.

11. The process of claim 10, wherein step (b) is conducted via a flow process.

12. The process of claim 3, wherein $P^1$ represents tert-butyloxycarbonyl (BOC), and step (c) comprises the use of Boc₂O in a solvent.

13. The process of claim 12, wherein the catalyst is Pd(OH)₂/C or Pd/Al₂O₃.

14. The process of claim 3, wherein $L_2$ represents a halogen atom.

15. The process of claim 14, wherein $L_2$ represents bromine or chlorine, and step (d) comprises the use of a base, selected from potassium carbonate, NaOMe, and t-BuOK, and a solvent, selected from acetonitrile, DMF, DMSO and a mixture of acetonitrile and formamide.

16. The process of claim 14, wherein $L_2$ represents bromine, or chlorine, and step (e) comprises the use of a base selected from potassium carbonate, NaOMe, t-BuOK, and t-BuONa, and a solvent selected from formamide and a mixture of DMF, DMSO, or acetonitrile with formamide.

17. The process of claim 1, further comprising preparing a compound of formula (VIII) from a compound of formula (VI):

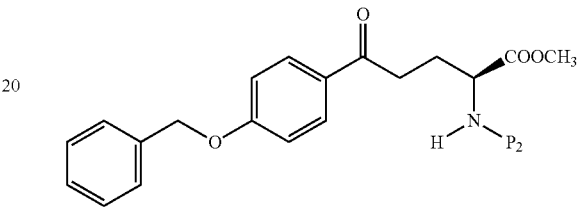

(VI)

Step (g)

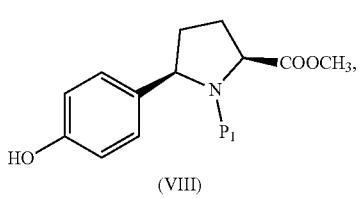

(VIII)

wherein $P_2$ is a protecting group selected from: tert-butyloxycarbonyl (BOC); 9-fluorenylmethyloxycarbonyl (FMOC); acetyl (Ac); benzoyl (Bz); carbamates; p-methoxyphenyl (PMP); tosyl (Ts); a sulfonamide selected from Nosyl and Nps, and trifluoroacetyl.

18. The process of claim 17, comprising:
preparing a compound of formula (VI) from a compound of formula (IV) by reacting the compound of formula (IV) with a compound of formula (V):

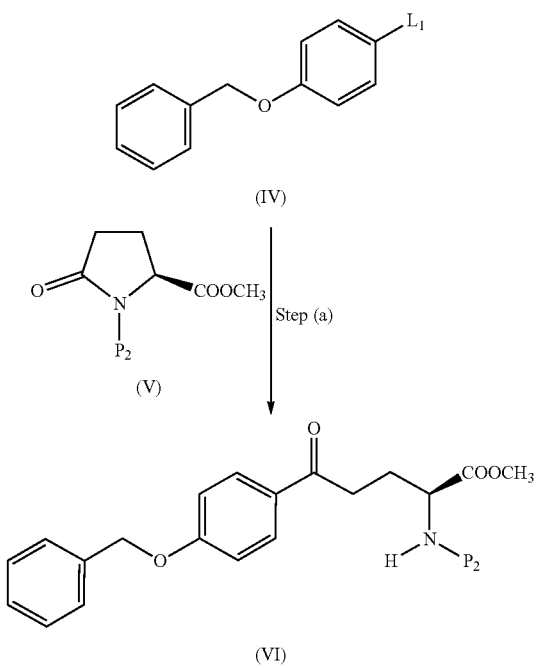

wherein
P₂ is a protecting group selected from: tert-butyloxycarbonyl (BOC); 9-fluorenylmethyloxycarbonyl (FMOC); acetyl (Ac); benzoyl (Bz); benzyloxycarbonyl; carbamates; p-methoxyphenyl (PMP); tosyl (Ts); a sulfonamide selected from Nosyl and Nps, and trifluoroacetyl, and
$L^1$ represents a leaving group.

19. The process of claim 18, further comprising preparing a compound of formula (II) by reacting a compound of formula (VIII) with a compound of formula (IX):

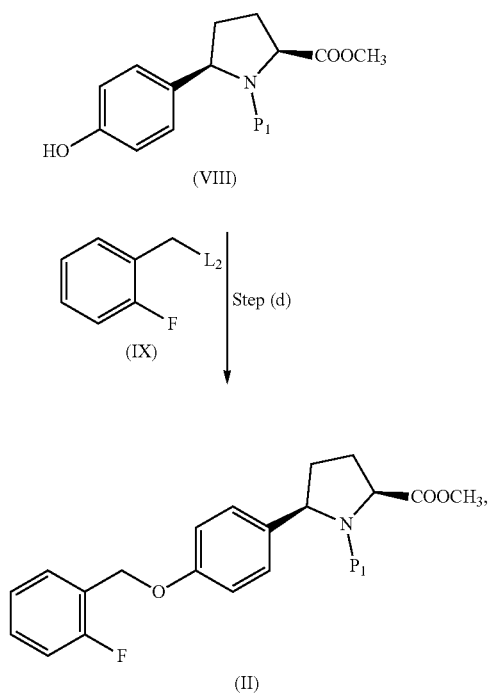

wherein $L_2$ represents a leaving group.

* * * * *